US012685775B2

(12) United States Patent
Evans et al.

(10) Patent No.: US 12,685,775 B2
(45) Date of Patent: Jul. 21, 2026

(54) OLIGONUCLEOTIDES WITH NUCLEOSIDE ANALOGS

(71) Applicant: Sirnaomics, Inc., Gatithersburg, MD (US)

(72) Inventors: David M. Evans, Gaithersburg, MD (US); Patrick Y. Lu, Gaithersburg, MD (US); Xiaoyong Lu, Gaithersburg, MD (US); Eric Roesch, Gaithersburg, MD (US)

(73) Assignee: SIRNAOMICS, INC., Gaithersburg, MD (US)

( * ) Notice: Subject to any disclaimer, the term of this patent is extended or adjusted under 35 U.S.C. 154(b) by 1011 days.

(21) Appl. No.: 17/713,025

(22) Filed: Apr. 4, 2022

(65) Prior Publication Data

US 2022/0387599 A1 Dec. 8, 2022

Related U.S. Application Data

(63) Continuation of application No. PCT/US2020/054093, filed on Oct. 2, 2020.

(60) Provisional application No. 62/977,630, filed on Feb. 17, 2020, provisional application No. 62/927,500, filed on Oct. 29, 2019, provisional application No. 62/909,526, filed on Oct. 2, 2019.

(51) Int. Cl.
| | |
|---|---|
| *C07H 21/04* | (2006.01) |
| *A61K 47/54* | (2017.01) |
| *A61K 47/55* | (2017.01) |
| *A61K 47/64* | (2017.01) |
| *A61P 35/00* | (2006.01) |

(52) U.S. Cl.
CPC .......... *A61K 47/549* (2017.08); *A61K 47/552* (2017.08); *A61K 47/641* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 2014/0088300 A1 | 3/2014 | Schmitz, Sr. et al. | |
| 2018/0251764 A1 | 9/2018 | Albaek et al. | |
| 2022/0145304 A1* | 5/2022 | Ju ..................... | A61K 31/7115 |

FOREIGN PATENT DOCUMENTS

| | | | |
|---|---|---|---|
| CN | 106906213 A | 6/2017 | |
| WO | 2012/070965 A1 | 5/2012 | |
| WO | WO-2015160770 A1 * | 10/2015 | ........... A61K 31/337 |
| WO | 2017/138925 A1 | 8/2017 | |
| WO | 2018/197490 A1 | 11/2018 | |

OTHER PUBLICATIONS

Sierant (New Journal of Chemistry, 2010, vol. 34, pp. 918-924). (Year: 2010).*
Ji et al (Cell Research, 2012, vol. 22: pp. 624-636). (Year: 2012).*
Fredebohm (Journal of Cell Science, 2013, vol. 126, pp. 3380-33-89). (Year: 2013).*
Zimmermann (Molecular Therapy, 2017, vol. 25, No. 1, pp. 71-78). (Year: 2017).*
Leng (Nucleic Acids Research, 2005, vol. 33, No. 4, pp. 1-9). (Year: 2005).*
International Search Report and the Written Opinion in PCT/US2020/054093, Feb. 4, 2021, 13 pages.
Extended European Search Report in corresponding EP Application No. 20871481.6, May 8, 2023, 10 pages.
Wonganan, P., et al., "Silencing of ribonucleotide reductase subunit M1 potentiates the antitumor activity of gemcitabine in resistant cancer cells", Cancer Biology and Therapy, vol. 13(10), 2012, pp. 908-914.
Ronco, C., et al., "ATM, ATR, CHK1, CHK2 and WEE1 inhibitors in cancer and cancer stem cells", Med. Chem. Commun., vol. 8(2), 2017, pp. 295-319.
Zuo, H., "iRGD: A Promising Peptide for Cancer Imaging and a Potential Therapeutic Agent for Various Cancers", Journal of Oncology, vol. 2019, 2019, pp. 1-15.
Park, J., et al., "Gemcitabine-Incorporated G-Quadruplex Aptamer for Targeted Drug Delivery into Pancreas Cancer", Molecular Therapy: Nucleic Acids, vol. 12, 2018, pp. 543-553.

* cited by examiner

*Primary Examiner* — Celine X Qian
(74) *Attorney, Agent, or Firm* — Edell, Shapiro & Finnan, LLC

(57) ABSTRACT siRNA compositions are provided that contain gemcitabine (GEM) in place of cytosine moieties within the siRNA sequence. Pharmaceuticals compositions containing these siRNA molecules, and methods of using the compositions for treating diseases such as cancer are provided.

10 Claims, 20 Drawing Sheets

Specification includes a Sequence Listing.

Figure 1  Basic structure
Blunt ended siRNA sequence shown
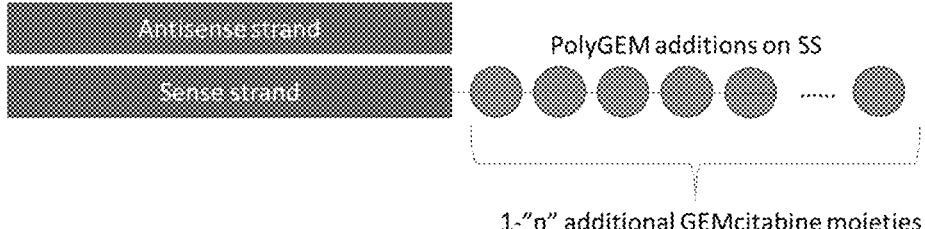
Figure 2 (a)   ASO sequence with a polyGEM tail
ASO sequence shown
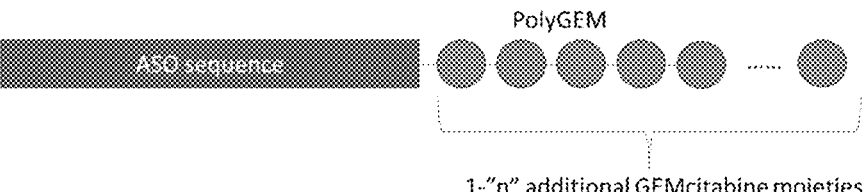
Figure 2 (b)   Targeted ASO delivery via a targeting ligand
ASO sequence shown
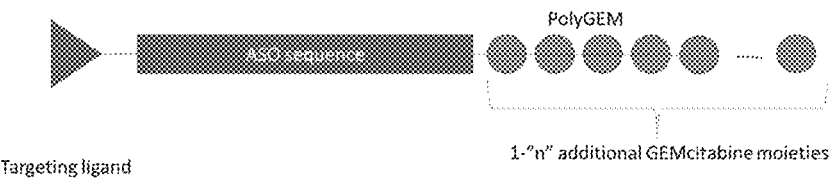
Figure 3 (a) Targeting ligand attached to Sense strand
Blunt ended siRNA sequence shown
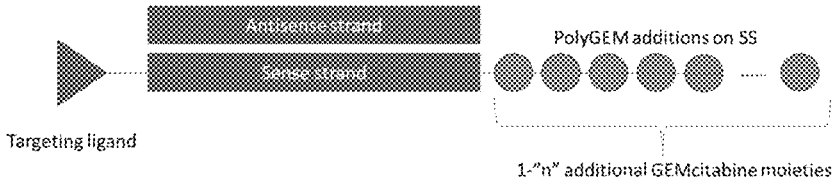

Figure 3 (b)   Targeting ligand attached to ASO strand
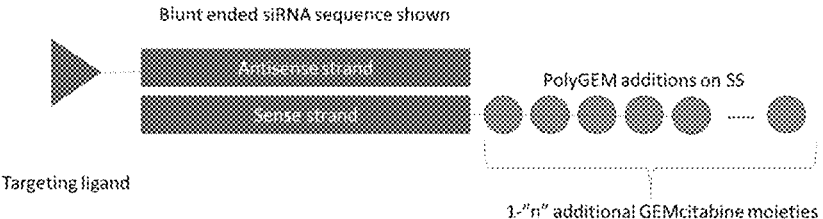
Figure 4   Equal length sense and antisense sequence with Gem-loop
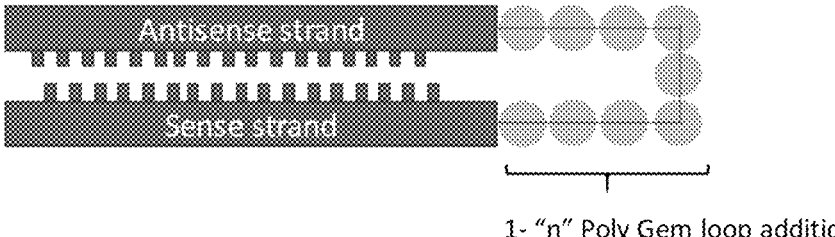
Figure 5   Non equal length sense sequence towards antisense with Gem-loop
Figure 6   Targeting delivery Equal length sequence with Gem-loop
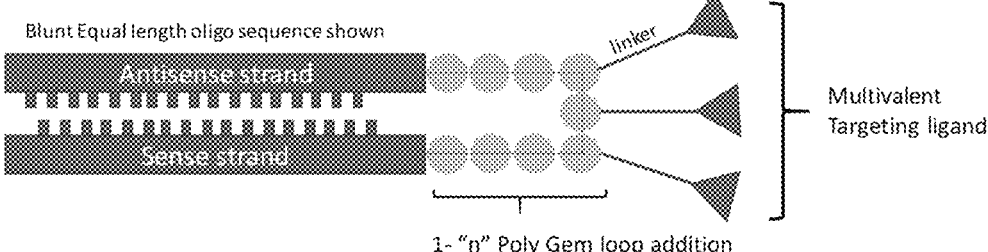

Figure 7   Targeting delivery non equal length sequence with Gem-loop
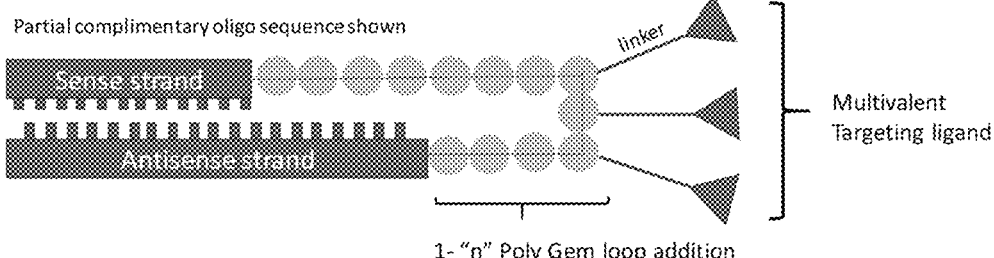

Figure 9. Sensitivity of Pancreatic cancer cell line viability upon transfection of a number of siRNA sequences designed against CHK1. Upper panel: BxPC3 cells, Lower panel: CFPAC cells
(a)
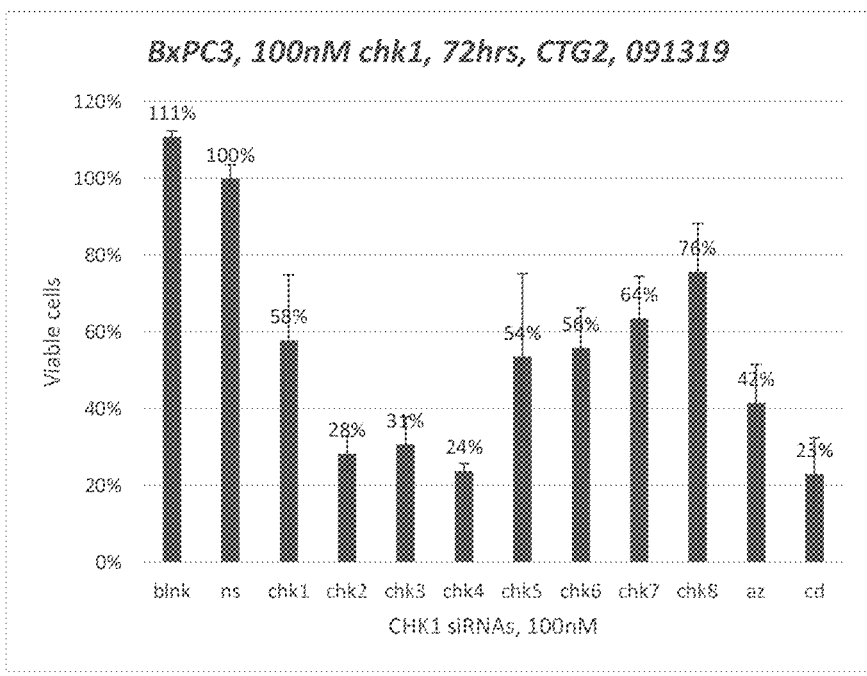
(b)
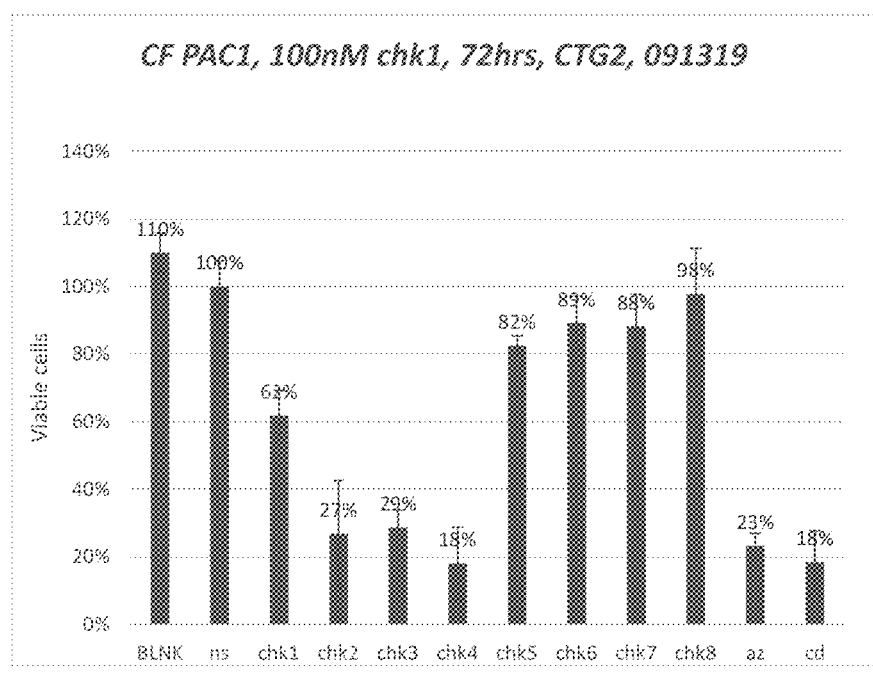

Figure 10

5-Fluorouracil    Gemcitabine    Acyclovir

ACV-TP-T

Figure 12 (a) P49-2 (CHK1_de_2GEM), P49-4 (RAD17/2GEM); GEM; CHK-az-25; and CHK-az-poly2
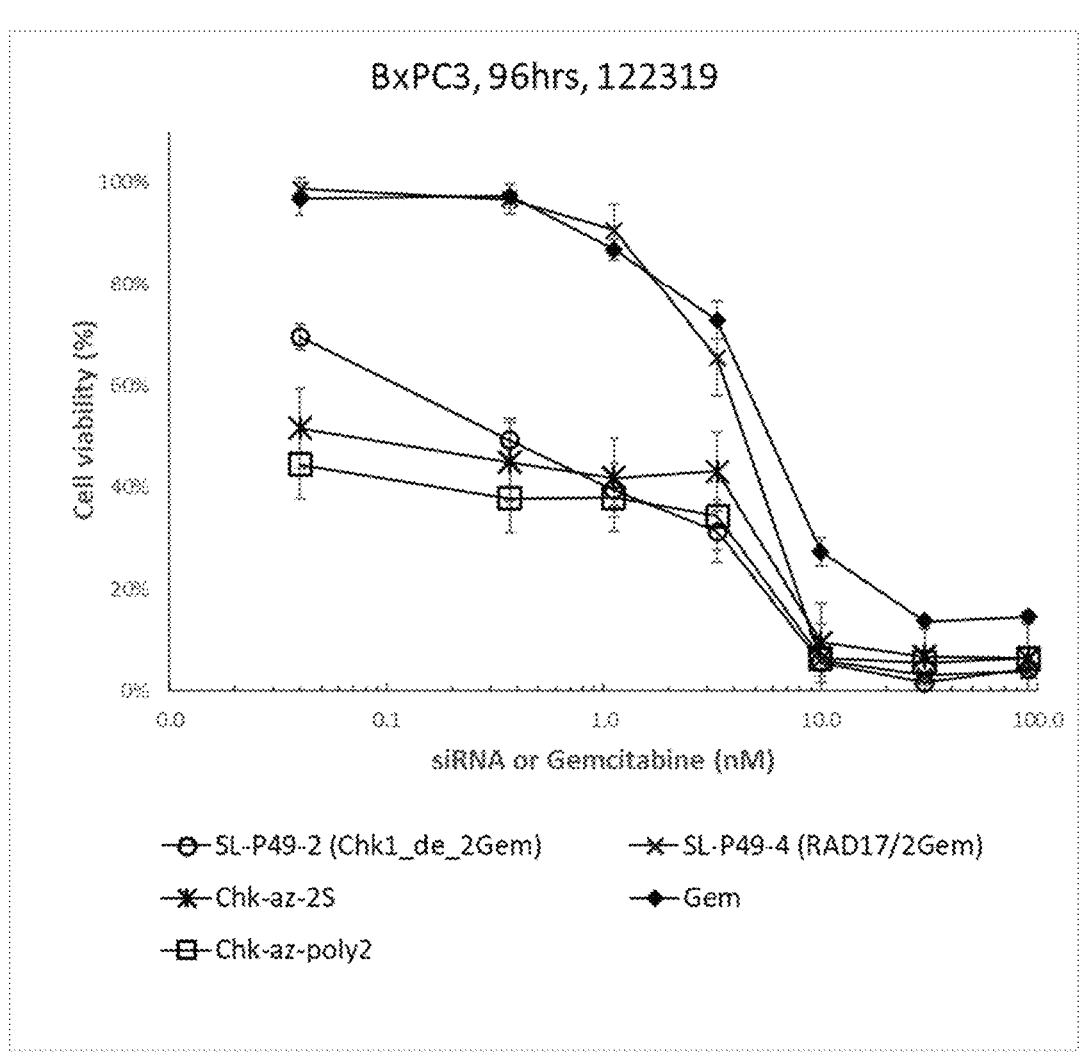

Figure 12 (b) P49-1 (CHK1_de); CHK-az; 2POlyG_az; P49-2 (CHK)de_2GEM; and GEM
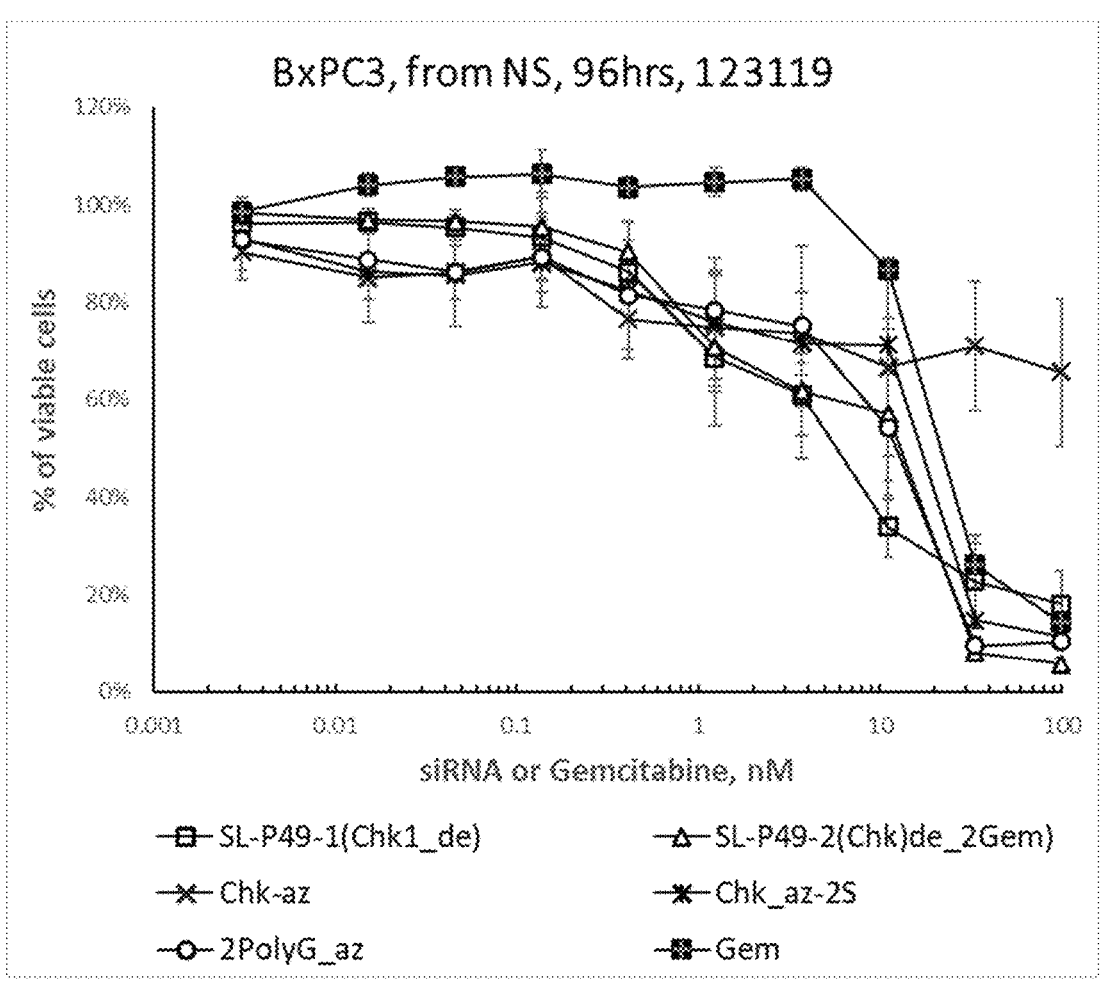

Figure 12 (c) P49-1 (CHK1_de), P49-7 (CHK1_de-full_4GEM); P49-4 (RAD17/2GEM); P49-2(CHK)de_2GEM; P49-3 (RAD17) and GEM
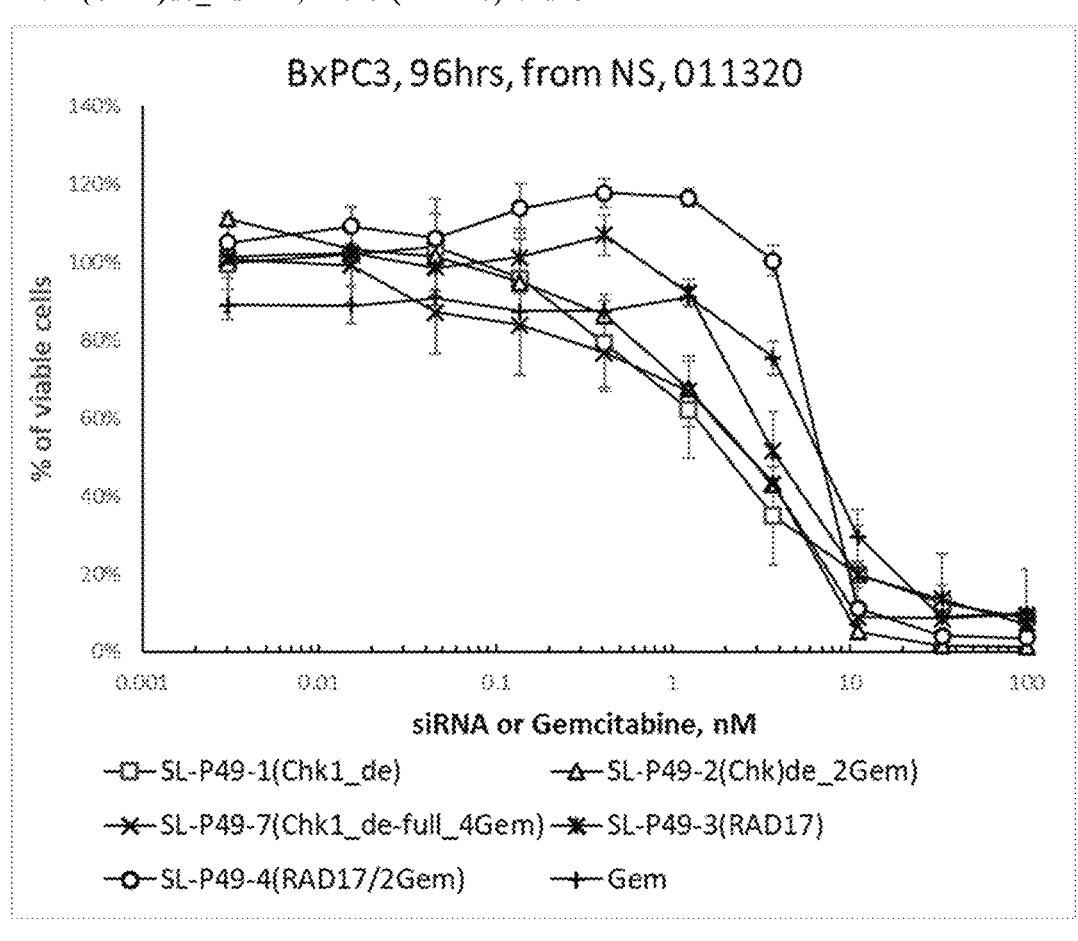

Figure 12 (d) P49-A (CHK1_de); CHK1az; 2PolyG_az; P49-2 (CHK1_de_2GWM); CHK_az-25; and GEM
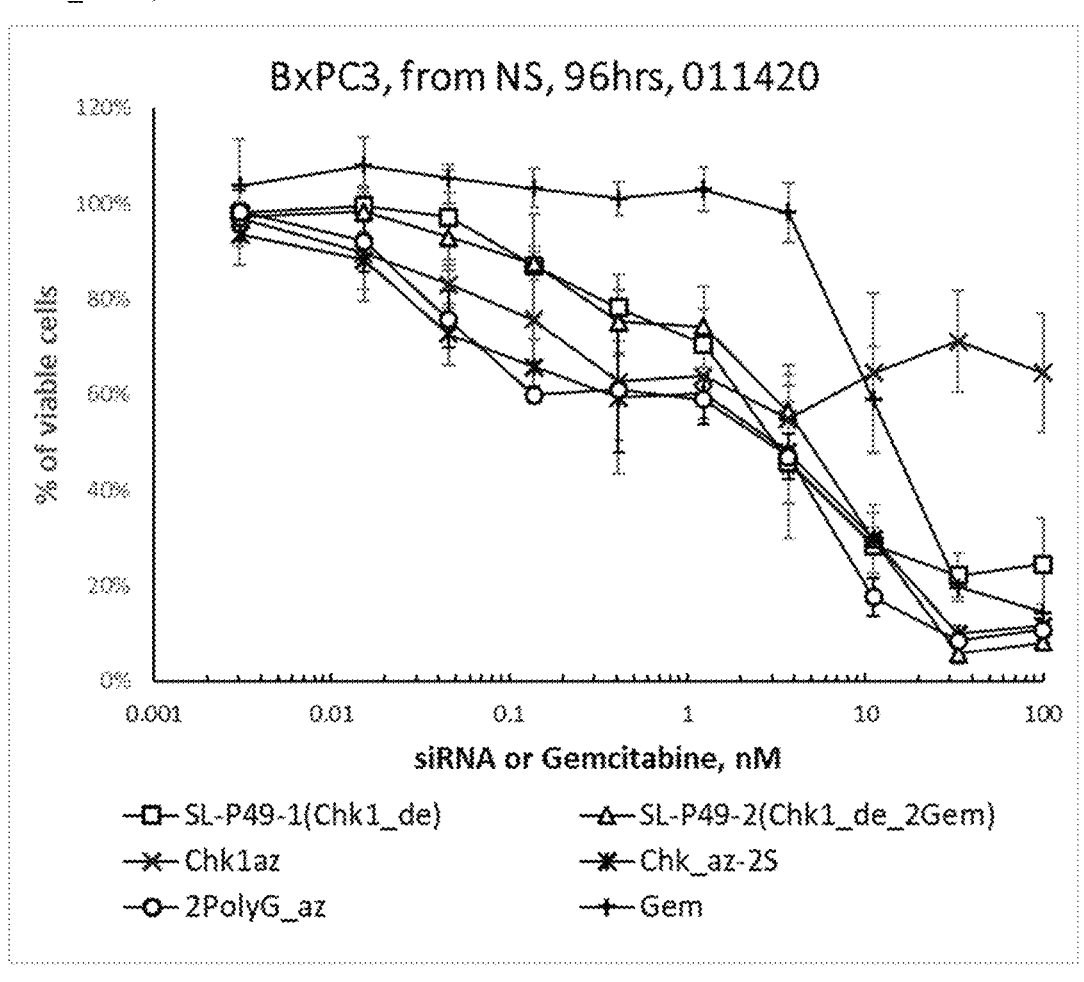

| | Chk1-az | Poly-2 | Poly-4 | Poly-6 | Gem |
|---|---|---|---|---|---|
| IC50 | 0.1620 | 0.02567 | 0.7419 | 0.3458 | 3.018 |

BxPC3_2A_2S_CID4_with NS CTRLs, CTG2_120hrs, 101619

| | 2A-Chk1 | 2A/NS | 2S/Chk1 | 2S/NS | CID4/Chk1 | CID4/NS |
|---|---|---|---|---|---|---|
| IC50 | 1.975 | 6.681 | 0.3496 | 5.424 | 1.807 | 5.189 |

SEQUENCE LISTING

```
<160> NUMBER OF SEQ ID NOS: 41

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 2', 2'-difluoro 2'-deoxycytidine
<220> FEATURE:
<221> NAME/KEY: modified_base
<222> LOCATION: (19)..(19)
<223> OTHER INFORMATION: 2', 2'-difluoro 2'-deoxycytidine
<220> FEATURE:
<221> NAME/KEY: modified_base
<222> LOCATION: (22)..(22)
<223> OTHER INFORMATION: 2', 2'-difluoro 2'-deoxycytidine

<400> SEQUENCE: 1
ccuguggaau aguacuuacu gcaau                                           25

<210> SEQ ID NO 2
<211> LENGTH: 25
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 2
auugcaguaa guacuauucc acagg                                          25

<210> SEQ ID NO 3
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 2', 2'-difluoro 2'-deoxycytidine
<220> FEATURE:
<221> NAME/KEY: modified_base
<222> LOCATION: (19)..(19)
<223> OTHER INFORMATION: 2', 2'-difluoro 2'-deoxycytidine
<220> FEATURE:
<221> NAME/KEY: modified_base
<222> LOCATION: (22)..(22)
<223> OTHER INFORMATION: 2', 2'-difluoro 2'-deoxycytidine
<220> FEATURE:
<221> NAME/KEY: modified_base
<222> LOCATION: (26)..(27)
<223> OTHER INFORMATION: 2', 2'-difluoro 2'-deoxycytidine

<400> SEQUENCE: 3
ccuguggaau aguacuuacu gcaaucc                                        27

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
auugauacag aucucuuucu u                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aagaaagaga ucuguaucaa u                                              21

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gggagaaggt gcctatggag aagtt                                          25

<210> SEQ ID NO 7
<211> LENGTH: 25
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggagaagttc aacttgctgt gaata                                            25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccagttgatg tttggtcctg tggaa                                            25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cctgtggaat agtacttact gcaat                                            25

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggaataactc acagggata                                                   19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gggatattaa accagaaaa                                                   19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcagaaccag ttgatgtttt                                                  19

<210> SEQ ID NO 13
<211> LENGTH: 19
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 13
ggaatagtac ttactgcaa                                                    19

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uuggaauaac uccacgggau a                                                 21

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(23)
<223> OTHER INFORMATION: 2', 2'-difluoro 2'-deoxycytidine

<400> SEQUENCE: 15
aagaaagaga ucuguaucaa ucctt                                             25

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(25)
<223> OTHER INFORMATION: 2', 2'-difluoro 2'-deoxycytidine

<400> SEQUENCE: 16
aagaaagaga ucuguaucaa ucccctt                                           27

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(27)
<223> OTHER INFORMATION: 2', 2'-difluoro 2'-deoxycytidine

<400> SEQUENCE: 17
```

-continued

```
aagaaagaga ucuguaucaa uccccccctt                                    29

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ccuguggaau aguacuuacu gcaau                                          25

<210> SEQ ID NO 19
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(27)
<223> OTHER INFORMATION: 2', 2'-difluoro 2'-deoxycytidine

<400> SEQUENCE: 19
ccuguggaau aguacuuacu gcaaucc                                        27

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2', 2'-difluoro 2'-deoxycytidine
<220> FEATURE:
<221> NAME/KEY: modified_base
<222> LOCATION: (17)..(17)
<223> OTHER INFORMATION: 2', 2'-difluoro 2'-deoxycytidine
<220> FEATURE:
<221> NAME/KEY: modified_base
<222> LOCATION: (20)..(20)
<223> OTHER INFORMATION: 2', 2'-difluoro 2'-deoxycytidine

<400> SEQUENCE: 20
uguggaauag uacuuacugc aau                                            23

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(25)
<223> OTHER INFORMATION: 2', 2'-difluoro 2'-deoxycytidine

<400> SEQUENCE: 21
uguggaauag uacuuacugc aaucc                                          25

<210> SEQ ID NO 22
<211> LENGTH: 25
<212> TYPE: RNA
```

-continued

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2', 2'-difluoro 2'-deoxycytidine
<220> FEATURE:
<221> NAME/KEY: modified_base
<222> LOCATION: (19)..(19)
<223> OTHER INFORMATION: 2', 2'-difluoro 2'-deoxycytidine
<220> FEATURE:
<221> NAME/KEY: modified_base
<222> LOCATION: (22)..(22)
<223> OTHER INFORMATION: 2', 2'-difluoro 2'-deoxycytidine

<400> SEQUENCE: 22
ccuguggaau aguacuuacu gcaau                                            25

<210> SEQ ID NO 23
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ccaacaauua ugaugaaauu ucuua                                            25

<210> SEQ ID NO 24
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(27)
<223> OTHER INFORMATION: 2', 2'-difluoro 2'-deoxycytidine

<400> SEQUENCE: 24
ccaacaauua ugaugaaauu ucuuacc                                          27

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
auugcaguaa guacuauucc acagg                                            25

<210> SEQ ID NO 26
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uaagaaauuu caucauaauu guugg                                            25

<210> SEQ ID NO 27
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Ala Val Pro Asn Leu Arg Gly Asp Leu Gln Val Leu Ala Gln Lys
1               5                   10                  15

Val Ala Arg Thr
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (20)..(20)
<223> OTHER INFORMATION: D-amino acid

<400> SEQUENCE: 28

Asn Ala Val Pro Asn Leu Arg Gly Asp Leu Gln Val Leu Ala Gln Lys
1               5                   10                  15

Val Ala Arg Thr
            20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (20)..(20)
<223> OTHER INFORMATION: D-amino acid

<400> SEQUENCE: 29

Asn Ala Val Pro Asn Leu Arg Gly Asp Leu Gln Val Leu Ala Gln Lys
1               5                   10                  15

Val Ala Arg Thr
            20

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
```

-continued

```
<223> OTHER INFORMATION: 2', 2'-difluoro 2'-deoxycytidine
<220> FEATURE:
<221> NAME/KEY: modified_base
<222> LOCATION: (18)..(18)
<223> OTHER INFORMATION: 2', 2'-difluoro 2'-deoxycytidine

<400> SEQUENCE: 30
aagaaagaga ucuguaucaa utt                                              23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
auugauacag aucucuuucu utt                                              23

<210> SEQ ID NO 32
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2', 2'-difluoro 2'-deoxycytidine
<220> FEATURE:
<221> NAME/KEY: modified_base
<222> LOCATION: (22)..(22)
<223> OTHER INFORMATION: 2', 2'-difluoro 2'-deoxycytidine

<400> SEQUENCE: 32
ccaacaauua ugaugaaauu ucuua                                            25

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys His His His Lys His His His Lys His His His Lys His His His
1               5                   10                  15

Lys

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys His His His Lys His His His Asn His His His Asn His His His
1               5                   10                  15

Asn
```

```
<210> SEQ ID NO 35
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MISC_FEATURE
<222> LOCATION: (2)..(6)
<223> OTHER INFORMATION: This region may encompass 1-5 residues
<220> FEATURE:
<221> NAME/KEY: MISC_FEATURE
<222> LOCATION: (7)..(9)
<223> OTHER INFORMATION: This region may encompass 0-3 residues
<220> FEATURE:
<221> NAME/KEY: MISC_FEATURE
<222> LOCATION: (10)..(14)
<223> OTHER INFORMATION: This region may encompass 1-5 residues
<220> FEATURE:
<221> NAME/KEY: MISC_FEATURE
<222> LOCATION: (15)..(17)
<223> OTHER INFORMATION: This region may encompass 0-3 residues
<220> FEATURE:
<221> NAME/KEY: MISC_FEATURE
<222> LOCATION: (18)..(22)
<223> OTHER INFORMATION: This region may encompass 1-5 residues
<220> FEATURE:
<221> NAME/KEY: MISC_FEATURE
<222> LOCATION: (23)..(25)
<223> OTHER INFORMATION: This region may encompass 0-3 residues
<220> FEATURE:
<221> NAME/KEY: MISC_FEATURE
<222> LOCATION: (26)..(30)
<223> OTHER INFORMATION: This region may encompass 1-5 residues
<220> FEATURE:
<221> NAME/KEY: MISC_FEATURE
<222> LOCATION: (31)..(33)
<223> OTHER INFORMATION: This region may encompass 0-3 residues
<220> FEATURE:
<221> NAME/KEY: MISC_FEATURE
<222> LOCATION: (34)..(38)
<223> OTHER INFORMATION: This region may encompass 1-5 residues
<220> FEATURE:
<221> NAME/KEY: MISC_FEATURE
<222> LOCATION: (39)..(41)
<223> OTHER INFORMATION: This region may encompass 0-3 residues
<220> FEATURE:
<221> NAME/KEY: MISC_FEATURE
<222> LOCATION: (42)..(46)
<223> OTHER INFORMATION: This region may encompass 1-5 residues
<220> FEATURE:
<221> NAME/KEY: MISC_FEATURE
<222> LOCATION: (47)..(49)
<223> OTHER INFORMATION: This region may encompass 0-3 residues
<220> FEATURE:
<221> NAME/KEY: MISC_FEATURE
<222> LOCATION: (50)..(54)
<223> OTHER INFORMATION: This region may encompass 1-5 residues
<220> FEATURE:
<221> NAME/KEY: MISC_FEATURE
<222> LOCATION: (55)..(57)
<223> OTHER INFORMATION: This region may encompass 0-3 residues
<220> FEATURE:
<221> NAME/KEY: MISC_FEATURE
<222> LOCATION: (58)..(62)
<223> OTHER INFORMATION: This region may encompass 1-5 residues
<220> FEATURE:
<221> NAME/KEY: MISC_FEATURE
<222> LOCATION: (63)..(65)
<223> OTHER INFORMATION: This region may encompass 0-3 residues
<220> FEATURE:
<221> NAME/KEY: MISC_FEATURE
<222> LOCATION: (66)..(70)
```

```
<223> OTHER INFORMATION: This region may encompass 1-5 residues
<220> FEATURE:
<221> NAME/KEY: MISC_FEATURE
<222> LOCATION: (71)..(73)
<223> OTHER INFORMATION: This region may encompass 0-3 residues
<220> FEATURE:
<221> NAME/KEY: MISC_FEATURE
<222> LOCATION: (74)..(78)
<223> OTHER INFORMATION: This region may encompass 1-5 residues
<220> FEATURE:
<221> NAME/KEY: MISC_FEATURE
<222> LOCATION: (79)..(81)
<223> OTHER INFORMATION: This region may encompass 0-3 residues
<220> FEATURE:
<221> NAME/KEY: MISC_FEATURE
<222> LOCATION: (2)..(81)
<223> OTHER INFORMATION: This region may encompass 3-10 "(H)n(K)m"
      units, wherein n = 1-5 and m = 0-3

<400> SEQUENCE: 35

Lys His His His His His Lys Lys Lys His His His His His Lys Lys
1               5                   10                  15

Lys His His His His His Lys Lys Lys His His His His His Lys Lys
            20                  25                  30

Lys His His His His His Lys Lys Lys His His His His His Lys Lys
        35                  40                  45

Lys His His His His His Lys Lys Lys His His His His His Lys Lys
    50                  55                  60

Lys His His His His His Lys Lys Lys His His His His His Lys Lys
65                  70                  75                  80

Lys

<210> SEQ ID NO 36
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MISC_FEATURE
<222> LOCATION: (2)..(6)
<223> OTHER INFORMATION: This region may encompass 1-5 residues
<220> FEATURE:
<221> NAME/KEY: MISC_FEATURE
<222> LOCATION: (7)..(9)
<223> OTHER INFORMATION: This region may encompass 0-3 residues
<220> FEATURE:
<221> NAME/KEY: MISC_FEATURE
<222> LOCATION: (10)..(14)
<223> OTHER INFORMATION: This region may encompass 1-5 residues
<220> FEATURE:
<221> NAME/KEY: MISC_FEATURE
<222> LOCATION: (15)..(17)
<223> OTHER INFORMATION: This region may encompass 0-3 residues
<220> FEATURE:
<221> NAME/KEY: MISC_FEATURE
<222> LOCATION: (18)..(22)
<223> OTHER INFORMATION: This region may encompass 1-5 residues
<220> FEATURE:
<221> NAME/KEY: MISC_FEATURE
<222> LOCATION: (23)..(25)
<223> OTHER INFORMATION: This region may encompass 0-3 residues
<220> FEATURE:
<221> NAME/KEY: MISC_FEATURE
<222> LOCATION: (26)..(30)
<223> OTHER INFORMATION: This region may encompass 1-5 residues
<220> FEATURE:
```

-continued

```
<221> NAME/KEY: MISC_FEATURE
<222> LOCATION: (31)..(33)
<223> OTHER INFORMATION: This region may encompass 0-3 residues
<220> FEATURE:
<221> NAME/KEY: MISC_FEATURE
<222> LOCATION: (34)..(38)
<223> OTHER INFORMATION: This region may encompass 1-5 residues
<220> FEATURE:
<221> NAME/KEY: MISC_FEATURE
<222> LOCATION: (39)..(41)
<223> OTHER INFORMATION: This region may encompass 0-3 residues
<220> FEATURE:
<221> NAME/KEY: MISC_FEATURE
<222> LOCATION: (42)..(46)
<223> OTHER INFORMATION: This region may encompass 1-5 residues
<220> FEATURE:
<221> NAME/KEY: MISC_FEATURE
<222> LOCATION: (47)..(49)
<223> OTHER INFORMATION: This region may encompass 0-3 residues
<220> FEATURE:
<221> NAME/KEY: MISC_FEATURE
<222> LOCATION: (50)..(54)
<223> OTHER INFORMATION: This region may encompass 1-5 residues
<220> FEATURE:
<221> NAME/KEY: MISC_FEATURE
<222> LOCATION: (55)..(57)
<223> OTHER INFORMATION: This region may encompass 0-3 residues
<220> FEATURE:
<221> NAME/KEY: MISC_FEATURE
<222> LOCATION: (58)..(62)
<223> OTHER INFORMATION: This region may encompass 1-5 residues
<220> FEATURE:
<221> NAME/KEY: MISC_FEATURE
<222> LOCATION: (63)..(65)
<223> OTHER INFORMATION: This region may encompass 0-3 residues
<220> FEATURE:
<221> NAME/KEY: MISC_FEATURE
<222> LOCATION: (66)..(70)
<223> OTHER INFORMATION: This region may encompass 1-5 residues
<220> FEATURE:
<221> NAME/KEY: MISC_FEATURE
<222> LOCATION: (71)..(73)
<223> OTHER INFORMATION: This region may encompass 0-3 residues
<220> FEATURE:
<221> NAME/KEY: MISC_FEATURE
<222> LOCATION: (74)..(78)
<223> OTHER INFORMATION: This region may encompass 1-5 residues
<220> FEATURE:
<221> NAME/KEY: MISC_FEATURE
<222> LOCATION: (79)..(81)
<223> OTHER INFORMATION: This region may encompass 0-3 residues
<220> FEATURE:
<221> NAME/KEY: MISC_FEATURE
<222> LOCATION: (2)..(81)
<223> OTHER INFORMATION: This region may encompass 3-10 "(H)n(K)m"
      units, wherein n = 1-5 and m = 0-3

<400> SEQUENCE: 36

Lys His His His His His Lys Lys Lys His His His His His Lys Lys
1               5                   10                  15

Lys His His His His His Lys Lys Lys His His His His His Lys Lys
            20                  25                  30

Lys His His His His His Lys Lys Lys His His His His His Lys Lys
        35                  40                      45

Lys His His His His His Lys Lys Lys His His His His His Lys Lys
    50                  55                  60

Lys His His His His His Lys Lys Lys His His His His His Lys Lys
65                  70                  75                  80

Lys Cys

<210> SEQ ID NO 37
<211> LENGTH: 281
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MISC_FEATURE
<222> LOCATION: (2)..(5)
<223> OTHER INFORMATION: This region may encompass 3 or 4 residues
<220> FEATURE:
<221> NAME/KEY: MISC_FEATURE
<222> LOCATION: (6)..(8)
<223> OTHER INFORMATION: This region may encompass 0-3 residues
<220> FEATURE:
<221> NAME/KEY: MISC_FEATURE
<222> LOCATION: (9)..(12)
<223> OTHER INFORMATION: This region may encompass 3 or 4 residues
<220> FEATURE:
<221> NAME/KEY: MISC_FEATURE
<222> LOCATION: (13)..(15)
<223> OTHER INFORMATION: This region may encompass 0-3 residues
<220> FEATURE:
<221> NAME/KEY: MISC_FEATURE
<222> LOCATION: (16)..(19)
<223> OTHER INFORMATION: This region may encompass 3 or 4 residues
<220> FEATURE:
<221> NAME/KEY: MISC_FEATURE
<222> LOCATION: (20)..(22)
<223> OTHER INFORMATION: This region may encompass 0-3 residues
<220> FEATURE:
<221> NAME/KEY: MISC_FEATURE
<222> LOCATION: (23)..(26)
<223> OTHER INFORMATION: This region may encompass 3 or 4 residues
<220> FEATURE:
<221> NAME/KEY: MISC_FEATURE
<222> LOCATION: (27)..(29)
<223> OTHER INFORMATION: This region may encompass 0-3 residues
<220> FEATURE:
<221> NAME/KEY: MISC_FEATURE
<222> LOCATION: (30)..(33)
<223> OTHER INFORMATION: This region may encompass 3 or 4 residues
<220> FEATURE:
<221> NAME/KEY: MISC_FEATURE
<222> LOCATION: (34)..(36)
<223> OTHER INFORMATION: This region may encompass 0-3 residues
<220> FEATURE:
<221> NAME/KEY: MISC_FEATURE
<222> LOCATION: (37)..(40)
<223> OTHER INFORMATION: This region may encompass 3 or 4 residues
<220> FEATURE:
<221> NAME/KEY: MISC_FEATURE
<222> LOCATION: (41)..(43)
<223> OTHER INFORMATION: This region may encompass 0-3 residues
<220> FEATURE:
<221> NAME/KEY: MISC_FEATURE
<222> LOCATION: (44)..(47)
<223> OTHER INFORMATION: This region may encompass 3 or 4 residues
<220> FEATURE:
<221> NAME/KEY: MISC_FEATURE
<222> LOCATION: (48)..(50)
<223> OTHER INFORMATION: This region may encompass 0-3 residues
<220> FEATURE:
<221> NAME/KEY: MISC_FEATURE
<222> LOCATION: (51)..(54)
<223> OTHER INFORMATION: This region may encompass 3 or 4 residues
<220> FEATURE:
<221> NAME/KEY: MISC_FEATURE
<222> LOCATION: (55)..(57)
<223> OTHER INFORMATION: This region may encompass 0-3 residues
<220> FEATURE:
<221> NAME/KEY: MISC_FEATURE
<222> LOCATION: (58)..(61)
<223> OTHER INFORMATION: This region may encompass 3 or 4 residues
<220> FEATURE:
<221> NAME/KEY: MISC_FEATURE
```

-continued

```
<222> LOCATION: (62)..(64)
<223> OTHER INFORMATION: This region may encompass 0-3 residues
<220> FEATURE:
<221> NAME/KEY: MISC_FEATURE
<222> LOCATION: (65)..(68)
<223> OTHER INFORMATION: This region may encompass 3 or 4 residues
<220> FEATURE:
<221> NAME/KEY: MISC_FEATURE
<222> LOCATION: (69)..(71)
<223> OTHER INFORMATION: This region may encompass 0-3 residues
<220> FEATURE:
<221> NAME/KEY: MISC_FEATURE
<222> LOCATION: (72)..(75)
<223> OTHER INFORMATION: This region may encompass 3 or 4 residues
<220> FEATURE:
<221> NAME/KEY: MISC_FEATURE
<222> LOCATION: (76)..(78)
<223> OTHER INFORMATION: This region may encompass 0-3 residues
<220> FEATURE:
<221> NAME/KEY: MISC_FEATURE
<222> LOCATION: (79)..(82)
<223> OTHER INFORMATION: This region may encompass 3 or 4 residues
<220> FEATURE:
<221> NAME/KEY: MISC_FEATURE
<222> LOCATION: (83)..(85)
<223> OTHER INFORMATION: This region may encompass 0-3 residues
<220> FEATURE:
<221> NAME/KEY: MISC_FEATURE
<222> LOCATION: (86)..(89)
<223> OTHER INFORMATION: This region may encompass 3 or 4 residues
<220> FEATURE:
<221> NAME/KEY: MISC_FEATURE
<222> LOCATION: (90)..(92)
<223> OTHER INFORMATION: This region may encompass 0-3 residues
<220> FEATURE:
<221> NAME/KEY: MISC_FEATURE
<222> LOCATION: (93)..(96)
<223> OTHER INFORMATION: This region may encompass 3 or 4 residues
<220> FEATURE:
<221> NAME/KEY: MISC_FEATURE
<222> LOCATION: (97)..(99)
<223> OTHER INFORMATION: This region may encompass 0-3 residues
<220> FEATURE:
<221> NAME/KEY: MISC_FEATURE
<222> LOCATION: (100)..(103)
<223> OTHER INFORMATION: This region may encompass 3 or 4 residues
<220> FEATURE:
<221> NAME/KEY: MISC_FEATURE
<222> LOCATION: (104)..(106)
<223> OTHER INFORMATION: This region may encompass 0-3 residues
<220> FEATURE:
<221> NAME/KEY: MISC_FEATURE
<222> LOCATION: (107)..(110)
<223> OTHER INFORMATION: This region may encompass 3 or 4 residues
<220> FEATURE:
<221> NAME/KEY: MISC_FEATURE
<222> LOCATION: (111)..(113)
<223> OTHER INFORMATION: This region may encompass 0-3 residues
<220> FEATURE:
<221> NAME/KEY: MISC_FEATURE
<222> LOCATION: (114)..(117)
<223> OTHER INFORMATION: This region may encompass 3 or 4 residues
<220> FEATURE:
<221> NAME/KEY: MISC_FEATURE
<222> LOCATION: (118)..(120)
<223> OTHER INFORMATION: This region may encompass 0-3 residues
<220> FEATURE:
<221> NAME/KEY: MISC_FEATURE
<222> LOCATION: (121)..(124)
<223> OTHER INFORMATION: This region may encompass 3 or 4 residues
<220> FEATURE:
<221> NAME/KEY: MISC_FEATURE
<222> LOCATION: (125)..(127)
<223> OTHER INFORMATION: This region may encompass 0-3 residues
<220> FEATURE:
<221> NAME/KEY: MISC_FEATURE
<222> LOCATION: (128)..(131)
<223> OTHER INFORMATION: This region may encompass 3 or 4 residues
<220> FEATURE:
```

-continued

```
<221> NAME/KEY: MISC_FEATURE
<222> LOCATION: (132)..(134)
<223> OTHER INFORMATION: This region may encompass 0-3 residues
<220> FEATURE:
<221> NAME/KEY: MISC_FEATURE
<222> LOCATION: (135)..(138)
<223> OTHER INFORMATION: This region may encompass 3 or 4 residues
<220> FEATURE:
<221> NAME/KEY: MISC_FEATURE
<222> LOCATION: (139)..(141)
<223> OTHER INFORMATION: This region may encompass 0-3 residues
<220> FEATURE:
<221> NAME/KEY: MISC_FEATURE
<222> LOCATION: (142)..(145)
<223> OTHER INFORMATION: This region may encompass 3 or 4 residues
<220> FEATURE:
<221> NAME/KEY: MISC_FEATURE
<222> LOCATION: (146)..(148)
<223> OTHER INFORMATION: This region may encompass 0-3 residues
<220> FEATURE:
<221> NAME/KEY: MISC_FEATURE
<222> LOCATION: (149)..(152)
<223> OTHER INFORMATION: This region may encompass 3 or 4 residues
<220> FEATURE:
<221> NAME/KEY: MISC_FEATURE
<222> LOCATION: (153)..(155)
<223> OTHER INFORMATION: This region may encompass 0-3 residues
<220> FEATURE:
<221> NAME/KEY: MISC_FEATURE
<222> LOCATION: (156)..(159)
<223> OTHER INFORMATION: This region may encompass 3 or 4 residues
<220> FEATURE:
<221> NAME/KEY: MISC_FEATURE
<222> LOCATION: (160)..(162)
<223> OTHER INFORMATION: This region may encompass 0-3 residues
<220> FEATURE:
<221> NAME/KEY: MISC_FEATURE
<222> LOCATION: (163)..(166)
<223> OTHER INFORMATION: This region may encompass 3 or 4 residues
<220> FEATURE:
<221> NAME/KEY: MISC_FEATURE
<222> LOCATION: (167)..(169)
<223> OTHER INFORMATION: This region may encompass 0-3 residues
<220> FEATURE:
<221> NAME/KEY: MISC_FEATURE
<222> LOCATION: (170)..(173)
<223> OTHER INFORMATION: This region may encompass 3 or 4 residues
<220> FEATURE:
<221> NAME/KEY: MISC_FEATURE
<222> LOCATION: (174)..(176)
<223> OTHER INFORMATION: This region may encompass 0-3 residues
<220> FEATURE:
<221> NAME/KEY: MISC_FEATURE
<222> LOCATION: (177)..(180)
<223> OTHER INFORMATION: This region may encompass 3 or 4 residues
<220> FEATURE:
<221> NAME/KEY: MISC_FEATURE
<222> LOCATION: (181)..(183)
<223> OTHER INFORMATION: This region may encompass 0-3 residues
<220> FEATURE:
<221> NAME/KEY: MISC_FEATURE
<222> LOCATION: (184)..(187)
<223> OTHER INFORMATION: This region may encompass 3 or 4 residues
<220> FEATURE:
<221> NAME/KEY: MISC_FEATURE
<222> LOCATION: (188)..(190)
<223> OTHER INFORMATION: This region may encompass 0-3 residues
<220> FEATURE:
<221> NAME/KEY: MISC_FEATURE
<222> LOCATION: (191)..(194)
<223> OTHER INFORMATION: This region may encompass 3 or 4 residues
<220> FEATURE:
<221> NAME/KEY: MISC_FEATURE
<222> LOCATION: (195)..(197)
<223> OTHER INFORMATION: This region may encompass 0-3 residues
<220> FEATURE:
<221> NAME/KEY: MISC_FEATURE
<222> LOCATION: (198)..(201)
<223> OTHER INFORMATION: This region may encompass 3 or 4 residues
```

-continued

```
<220> FEATURE:
<221> NAME/KEY: MISC_FEATURE
<222> LOCATION: (202)..(204)
<223> OTHER INFORMATION: This region may encompass 0-3 residues
<220> FEATURE:
<221> NAME/KEY: MISC_FEATURE
<222> LOCATION: (205)..(208)
<223> OTHER INFORMATION: This region may encompass 3 or 4 residues
<220> FEATURE:
<221> NAME/KEY: MISC_FEATURE
<222> LOCATION: (209)..(211)
<223> OTHER INFORMATION: This region may encompass 0-3 residues
<220> FEATURE:
<221> NAME/KEY: MISC_FEATURE
<222> LOCATION: (212)..(215)
<223> OTHER INFORMATION: This region may encompass 3 or 4 residues
<220> FEATURE:
<221> NAME/KEY: MISC_FEATURE
<222> LOCATION: (216)..(218)
<223> OTHER INFORMATION: This region may encompass 0-3 residues
<220> FEATURE:
<221> NAME/KEY: MISC_FEATURE
<222> LOCATION: (219)..(222)
<223> OTHER INFORMATION: This region may encompass 3 or 4 residues
<220> FEATURE:
<221> NAME/KEY: MISC_FEATURE
<222> LOCATION: (223)..(225)
<223> OTHER INFORMATION: This region may encompass 0-3 residues
<220> FEATURE:
<221> NAME/KEY: MISC_FEATURE
<222> LOCATION: (226)..(229)
<223> OTHER INFORMATION: This region may encompass 3 or 4 residues
<220> FEATURE:
<221> NAME/KEY: MISC_FEATURE
<222> LOCATION: (230)..(232)
<223> OTHER INFORMATION: This region may encompass 0-3 residues
<220> FEATURE:
<221> NAME/KEY: MISC_FEATURE
<222> LOCATION: (233)..(236)
<223> OTHER INFORMATION: This region may encompass 3 or 4 residues
<220> FEATURE:
<221> NAME/KEY: MISC_FEATURE
<222> LOCATION: (237)..(239)
<223> OTHER INFORMATION: This region may encompass 0-3 residues
<220> FEATURE:
<221> NAME/KEY: MISC_FEATURE
<222> LOCATION: (240)..(243)
<223> OTHER INFORMATION: This region may encompass 3 or 4 residues
<220> FEATURE:
<221> NAME/KEY: MISC_FEATURE
<222> LOCATION: (244)..(246)
<223> OTHER INFORMATION: This region may encompass 0-3 residues
<220> FEATURE:
<221> NAME/KEY: MISC_FEATURE
<222> LOCATION: (247)..(250)
<223> OTHER INFORMATION: This region may encompass 3 or 4 residues
<220> FEATURE:
<221> NAME/KEY: MISC_FEATURE
<222> LOCATION: (251)..(253)
<223> OTHER INFORMATION: This region may encompass 0-3 residues
<220> FEATURE:
<221> NAME/KEY: MISC_FEATURE
<222> LOCATION: (254)..(257)
<223> OTHER INFORMATION: This region may encompass 3 or 4 residues
<220> FEATURE:
<221> NAME/KEY: MISC_FEATURE
<222> LOCATION: (258)..(260)
<223> OTHER INFORMATION: This region may encompass 0-3 residues
<220> FEATURE:
<221> NAME/KEY: MISC_FEATURE
<222> LOCATION: (261)..(264)
<223> OTHER INFORMATION: This region may encompass 3 or 4 residues
<220> FEATURE:
<221> NAME/KEY: MISC_FEATURE
<222> LOCATION: (265)..(267)
<223> OTHER INFORMATION: This region may encompass 0-3 residues
<220> FEATURE:
<221> NAME/KEY: MISC_FEATURE
<222> LOCATION: (268)..(271)
```

```
<223> OTHER INFORMATION: This region may encompass 3 or 4 residues
<220> FEATURE:
<221> NAME/KEY: MISC_FEATURE
<222> LOCATION: (272)..(274)
<223> OTHER INFORMATION: This region may encompass 0-3 residues
<220> FEATURE:
<221> NAME/KEY: MISC_FEATURE
<222> LOCATION: (275)..(278)
<223> OTHER INFORMATION: This region may encompass 3 or 4 residues
<220> FEATURE:
<221> NAME/KEY: MISC_FEATURE
<222> LOCATION: (279)..(281)
<223> OTHER INFORMATION: This region may encompass 0-3 residues
<220> FEATURE:
<221> NAME/KEY: MISC_FEATURE
<222> LOCATION: (2)..(281)
<223> OTHER INFORMATION: This region may encompass 3-10
        "(H)a(K)m(H)b(K)m(H)c(K)m(H)d(K)m" units, wherein a, b, c, and
        d = 3 or 4 and m = 0-3

<400> SEQUENCE: 37

Lys His His His His Lys Lys Lys His His His His Lys Lys Lys His
1               5                   10                  15

His His His Lys Lys Lys His His His His Lys Lys Lys His His His
                20                  25                  30

His Lys Lys Lys His His His His Lys Lys Lys His His His His Lys
        35                  40                  45

Lys Lys His His His His Lys Lys Lys His His His His Lys Lys Lys
        50                  55                  60

His His His His Lys Lys Lys His His His His Lys Lys Lys His His
65                  70                  75                  80

His His Lys Lys Lys His His His His Lys Lys Lys His His His His
                85                  90                  95

Lys Lys Lys His His His His Lys Lys Lys His His His His Lys Lys
                100                 105                 110

Lys His His His His Lys Lys Lys His His His His Lys Lys Lys His
                115                 120                 125

His His His Lys Lys Lys His His His His Lys Lys Lys His His His
        130                 135                 140

His Lys Lys Lys His His His His Lys Lys Lys His His His His Lys
145                 150                 155                 160

Lys Lys His His His His Lys Lys Lys His His His His Lys Lys Lys
        165                 170                 175

His His His His Lys Lys Lys His His His His Lys Lys Lys His His
        180                 185                 190

His His Lys Lys Lys His His His His Lys Lys Lys His His His His
        195                 200                 205

Lys Lys Lys His His His His Lys Lys Lys His His His His Lys Lys
        210                 215                 220

Lys His His His His Lys Lys Lys His His His His Lys Lys Lys His
225                 230                 235                 240

His His His Lys Lys Lys His His His His Lys Lys Lys His His His
        245                 250                 255

His Lys Lys Lys His His His His Lys Lys Lys His His His His Lys
        260                 265                 270

Lys Lys His His His His Lys Lys Lys
        275                 280

<210> SEQ ID NO 38
<211> LENGTH: 282
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MISC_FEATURE
<222> LOCATION: (2)..(5)
<223> OTHER INFORMATION: This region may encompass 3 or 4 residues
<220> FEATURE:
<221> NAME/KEY: MISC_FEATURE
<222> LOCATION: (6)..(8)
<223> OTHER INFORMATION: This region may encompass 0-3 residues
<220> FEATURE:
<221> NAME/KEY: MISC_FEATURE
<222> LOCATION: (9)..(12)
<223> OTHER INFORMATION: This region may encompass 3 or 4 residues
<220> FEATURE:
<221> NAME/KEY: MISC_FEATURE
<222> LOCATION: (13)..(15)
<223> OTHER INFORMATION: This region may encompass 0-3 residues
<220> FEATURE:
<221> NAME/KEY: MISC_FEATURE
<222> LOCATION: (16)..(19)
<223> OTHER INFORMATION: This region may encompass 3 or 4 residues
<220> FEATURE:
<221> NAME/KEY: MISC_FEATURE
<222> LOCATION: (20)..(22)
<223> OTHER INFORMATION: This region may encompass 0-3 residues
<220> FEATURE:
<221> NAME/KEY: MISC_FEATURE
<222> LOCATION: (23)..(26)
<223> OTHER INFORMATION: This region may encompass 3 or 4 residues
<220> FEATURE:
<221> NAME/KEY: MISC_FEATURE
<222> LOCATION: (27)..(29)
<223> OTHER INFORMATION: This region may encompass 0-3 residues
<220> FEATURE:
<221> NAME/KEY: MISC_FEATURE
<222> LOCATION: (30)..(33)
<223> OTHER INFORMATION: This region may encompass 3 or 4 residues
<220> FEATURE:
<221> NAME/KEY: MISC_FEATURE
<222> LOCATION: (34)..(36)
<223> OTHER INFORMATION: This region may encompass 0-3 residues
<220> FEATURE:
<221> NAME/KEY: MISC_FEATURE
<222> LOCATION: (37)..(40)
<223> OTHER INFORMATION: This region may encompass 3 or 4 residues
<220> FEATURE:
<221> NAME/KEY: MISC_FEATURE
<222> LOCATION: (41)..(43)
<223> OTHER INFORMATION: This region may encompass 0-3 residues
<220> FEATURE:
<221> NAME/KEY: MISC_FEATURE
<222> LOCATION: (44)..(47)
<223> OTHER INFORMATION: This region may encompass 3 or 4 residues
<220> FEATURE:
<221> NAME/KEY: MISC_FEATURE
<222> LOCATION: (48)..(50)
<223> OTHER INFORMATION: This region may encompass 0-3 residues
<220> FEATURE:
<221> NAME/KEY: MISC_FEATURE
<222> LOCATION: (51)..(54)
<223> OTHER INFORMATION: This region may encompass 3 or 4 residues
<220> FEATURE:
<221> NAME/KEY: MISC_FEATURE
<222> LOCATION: (55)..(57)
<223> OTHER INFORMATION: This region may encompass 0-3 residues
<220> FEATURE:
<221> NAME/KEY: MISC_FEATURE
<222> LOCATION: (58)..(61)
<223> OTHER INFORMATION: This region may encompass 3 or 4 residues
<220> FEATURE:
<221> NAME/KEY: MISC_FEATURE
```

```
<222> LOCATION: (62)..(64)
<223> OTHER INFORMATION: This region may encompass 0-3 residues
<220> FEATURE:
<221> NAME/KEY: MISC_FEATURE
<222> LOCATION: (65)..(68)
<223> OTHER INFORMATION: This region may encompass 3 or 4 residues
<220> FEATURE:
<221> NAME/KEY: MISC_FEATURE
<222> LOCATION: (69)..(71)
<223> OTHER INFORMATION: This region may encompass 0-3 residues
<220> FEATURE:
<221> NAME/KEY: MISC_FEATURE
<222> LOCATION: (72)..(75)
<223> OTHER INFORMATION: This region may encompass 3 or 4 residues
<220> FEATURE:
<221> NAME/KEY: MISC_FEATURE
<222> LOCATION: (76)..(78)
<223> OTHER INFORMATION: This region may encompass 0-3 residues
<220> FEATURE:
<221> NAME/KEY: MISC_FEATURE
<222> LOCATION: (79)..(82)
<223> OTHER INFORMATION: This region may encompass 3 or 4 residues
<220> FEATURE:
<221> NAME/KEY: MISC_FEATURE
<222> LOCATION: (83)..(85)
<223> OTHER INFORMATION: This region may encompass 0-3 residues
<220> FEATURE:
<221> NAME/KEY: MISC_FEATURE
<222> LOCATION: (86)..(89)
<223> OTHER INFORMATION: This region may encompass 3 or 4 residues
<220> FEATURE:
<221> NAME/KEY: MISC_FEATURE
<222> LOCATION: (90)..(92)
<223> OTHER INFORMATION: This region may encompass 0-3 residues
<220> FEATURE:
<221> NAME/KEY: MISC_FEATURE
<222> LOCATION: (93)..(96)
<223> OTHER INFORMATION: This region may encompass 3 or 4 residues
<220> FEATURE:
<221> NAME/KEY: MISC_FEATURE
<222> LOCATION: (97)..(99)
<223> OTHER INFORMATION: This region may encompass 0-3 residues
<220> FEATURE:
<221> NAME/KEY: MISC_FEATURE
<222> LOCATION: (100)..(103)
<223> OTHER INFORMATION: This region may encompass 3 or 4 residues
<220> FEATURE:
<221> NAME/KEY: MISC_FEATURE
<222> LOCATION: (104)..(106)
<223> OTHER INFORMATION: This region may encompass 0-3 residues
<220> FEATURE:
<221> NAME/KEY: MISC_FEATURE
<222> LOCATION: (107)..(110)
<223> OTHER INFORMATION: This region may encompass 3 or 4 residues
<220> FEATURE:
<221> NAME/KEY: MISC_FEATURE
<222> LOCATION: (111)..(113)
<223> OTHER INFORMATION: This region may encompass 0-3 residues
<220> FEATURE:
<221> NAME/KEY: MISC_FEATURE
<222> LOCATION: (114)..(117)
<223> OTHER INFORMATION: This region may encompass 3 or 4 residues
<220> FEATURE:
<221> NAME/KEY: MISC_FEATURE
<222> LOCATION: (118)..(120)
<223> OTHER INFORMATION: This region may encompass 0-3 residues
<220> FEATURE:
<221> NAME/KEY: MISC_FEATURE
<222> LOCATION: (121)..(124)
<223> OTHER INFORMATION: This region may encompass 3 or 4 residues
<220> FEATURE:
<221> NAME/KEY: MISC_FEATURE
<222> LOCATION: (125)..(127)
<223> OTHER INFORMATION: This region may encompass 0-3 residues
<220> FEATURE:
<221> NAME/KEY: MISC_FEATURE
<222> LOCATION: (128)..(131)
<223> OTHER INFORMATION: This region may encompass 3 or 4 residues
<220> FEATURE:
```

-continued

```
<221> NAME/KEY: MISC_FEATURE
<222> LOCATION: (132)..(134)
<223> OTHER INFORMATION: This region may encompass 0-3 residues
<220> FEATURE:
<221> NAME/KEY: MISC_FEATURE
<222> LOCATION: (135)..(138)
<223> OTHER INFORMATION: This region may encompass 3 or 4 residues
<220> FEATURE:
<221> NAME/KEY: MISC_FEATURE
<222> LOCATION: (139)..(141)
<223> OTHER INFORMATION: This region may encompass 0-3 residues
<220> FEATURE:
<221> NAME/KEY: MISC_FEATURE
<222> LOCATION: (142)..(145)
<223> OTHER INFORMATION: This region may encompass 3 or 4 residues
<220> FEATURE:
<221> NAME/KEY: MISC_FEATURE
<222> LOCATION: (146)..(148)
<223> OTHER INFORMATION: This region may encompass 0-3 residues
<220> FEATURE:
<221> NAME/KEY: MISC_FEATURE
<222> LOCATION: (149)..(152)
<223> OTHER INFORMATION: This region may encompass 3 or 4 residues
<220> FEATURE:
<221> NAME/KEY: MISC_FEATURE
<222> LOCATION: (153)..(155)
<223> OTHER INFORMATION: This region may encompass 0-3 residues
<220> FEATURE:
<221> NAME/KEY: MISC_FEATURE
<222> LOCATION: (156)..(159)
<223> OTHER INFORMATION: This region may encompass 3 or 4 residues
<220> FEATURE:
<221> NAME/KEY: MISC_FEATURE
<222> LOCATION: (160)..(162)
<223> OTHER INFORMATION: This region may encompass 0-3 residues
<220> FEATURE:
<221> NAME/KEY: MISC_FEATURE
<222> LOCATION: (163)..(166)
<223> OTHER INFORMATION: This region may encompass 3 or 4 residues
<220> FEATURE:
<221> NAME/KEY: MISC_FEATURE
<222> LOCATION: (167)..(169)
<223> OTHER INFORMATION: This region may encompass 0-3 residues
<220> FEATURE:
<221> NAME/KEY: MISC_FEATURE
<222> LOCATION: (170)..(173)
<223> OTHER INFORMATION: This region may encompass 3 or 4 residues
<220> FEATURE:
<221> NAME/KEY: MISC_FEATURE
<222> LOCATION: (174)..(176)
<223> OTHER INFORMATION: This region may encompass 0-3 residues
<220> FEATURE:
<221> NAME/KEY: MISC_FEATURE
<222> LOCATION: (177)..(180)
<223> OTHER INFORMATION: This region may encompass 3 or 4 residues
<220> FEATURE:
<221> NAME/KEY: MISC_FEATURE
<222> LOCATION: (181)..(183)
<223> OTHER INFORMATION: This region may encompass 0-3 residues
<220> FEATURE:
<221> NAME/KEY: MISC_FEATURE
<222> LOCATION: (184)..(187)
<223> OTHER INFORMATION: This region may encompass 3 or 4 residues
<220> FEATURE:
<221> NAME/KEY: MISC_FEATURE
<222> LOCATION: (188)..(190)
<223> OTHER INFORMATION: This region may encompass 0-3 residues
<220> FEATURE:
<221> NAME/KEY: MISC_FEATURE
<222> LOCATION: (191)..(194)
<223> OTHER INFORMATION: This region may encompass 3 or 4 residues
<220> FEATURE:
<221> NAME/KEY: MISC_FEATURE
<222> LOCATION: (195)..(197)
<223> OTHER INFORMATION: This region may encompass 0-3 residues
<220> FEATURE:
<221> NAME/KEY: MISC_FEATURE
<222> LOCATION: (198)..(201)
<223> OTHER INFORMATION: This region may encompass 3 or 4 residues
```

-continued

```
<220> FEATURE:
<221> NAME/KEY: MISC_FEATURE
<222> LOCATION: (202)..(204)
<223> OTHER INFORMATION: This region may encompass 0-3 residues
<220> FEATURE:
<221> NAME/KEY: MISC_FEATURE
<222> LOCATION: (205)..(208)
<223> OTHER INFORMATION: This region may encompass 3 or 4 residues
<220> FEATURE:
<221> NAME/KEY: MISC_FEATURE
<222> LOCATION: (209)..(211)
<223> OTHER INFORMATION: This region may encompass 0-3 residues
<220> FEATURE:
<221> NAME/KEY: MISC_FEATURE
<222> LOCATION: (212)..(215)
<223> OTHER INFORMATION: This region may encompass 3 or 4 residues
<220> FEATURE:
<221> NAME/KEY: MISC_FEATURE
<222> LOCATION: (216)..(218)
<223> OTHER INFORMATION: This region may encompass 0-3 residues
<220> FEATURE:
<221> NAME/KEY: MISC_FEATURE
<222> LOCATION: (219)..(222)
<223> OTHER INFORMATION: This region may encompass 3 or 4 residues
<220> FEATURE:
<221> NAME/KEY: MISC_FEATURE
<222> LOCATION: (223)..(225)
<223> OTHER INFORMATION: This region may encompass 0-3 residues
<220> FEATURE:
<221> NAME/KEY: MISC_FEATURE
<222> LOCATION: (226)..(229)
<223> OTHER INFORMATION: This region may encompass 3 or 4 residues
<220> FEATURE:
<221> NAME/KEY: MISC_FEATURE
<222> LOCATION: (230)..(232)
<223> OTHER INFORMATION: This region may encompass 0-3 residues
<220> FEATURE:
<221> NAME/KEY: MISC_FEATURE
<222> LOCATION: (233)..(236)
<223> OTHER INFORMATION: This region may encompass 3 or 4 residues
<220> FEATURE:
<221> NAME/KEY: MISC_FEATURE
<222> LOCATION: (237)..(239)
<223> OTHER INFORMATION: This region may encompass 0-3 residues
<220> FEATURE:
<221> NAME/KEY: MISC_FEATURE
<222> LOCATION: (240)..(243)
<223> OTHER INFORMATION: This region may encompass 3 or 4 residues
<220> FEATURE:
<221> NAME/KEY: MISC_FEATURE
<222> LOCATION: (244)..(246)
<223> OTHER INFORMATION: This region may encompass 0-3 residues
<220> FEATURE:
<221> NAME/KEY: MISC_FEATURE
<222> LOCATION: (247)..(250)
<223> OTHER INFORMATION: This region may encompass 3 or 4 residues
<220> FEATURE:
<221> NAME/KEY: MISC_FEATURE
<222> LOCATION: (251)..(253)
<223> OTHER INFORMATION: This region may encompass 0-3 residues
<220> FEATURE:
<221> NAME/KEY: MISC_FEATURE
<222> LOCATION: (254)..(257)
<223> OTHER INFORMATION: This region may encompass 3 or 4 residues
<220> FEATURE:
<221> NAME/KEY: MISC_FEATURE
<222> LOCATION: (258)..(260)
<223> OTHER INFORMATION: This region may encompass 0-3 residues
<220> FEATURE:
<221> NAME/KEY: MISC_FEATURE
<222> LOCATION: (261)..(264)
<223> OTHER INFORMATION: This region may encompass 3 or 4 residues
<220> FEATURE:
<221> NAME/KEY: MISC_FEATURE
<222> LOCATION: (265)..(267)
<223> OTHER INFORMATION: This region may encompass 0-3 residues
<220> FEATURE:
<221> NAME/KEY: MISC_FEATURE
<222> LOCATION: (268)..(271)
```

```
<223> OTHER INFORMATION: This region may encompass 3 or 4 residues
<220> FEATURE:
<221> NAME/KEY: MISC_FEATURE
<222> LOCATION: (272)..(274)
<223> OTHER INFORMATION: This region may encompass 0-3 residues
<220> FEATURE:
<221> NAME/KEY: MISC_FEATURE
<222> LOCATION: (275)..(278)
<223> OTHER INFORMATION: This region may encompass 3 or 4 residues
<220> FEATURE:
<221> NAME/KEY: MISC_FEATURE
<222> LOCATION: (279)..(281)
<223> OTHER INFORMATION: This region may encompass 0-3 residues
<220> FEATURE:
<221> NAME/KEY: MISC_FEATURE
<222> LOCATION: (2)..(281)
<223> OTHER INFORMATION: This region may encompass 3-10
         "(H)a(K)m(H)b(K)m(H)c(K)m(H)d(K)m" units, wherein a, b, c, and
         d = 3 or 4 and m = 0-3

<400> SEQUENCE: 38

Lys His His His His Lys Lys Lys His His His His Lys Lys Lys His
1               5                   10                  15

His His His Lys Lys Lys His His His His Lys Lys Lys His His His
                20                  25                  30

His Lys Lys Lys His His His His Lys Lys Lys His His His His Lys
        35                  40                  45

Lys Lys His His His His Lys Lys Lys His His His His Lys Lys Lys
        50                  55                  60

His His His His Lys Lys Lys His His His His Lys Lys Lys His His
65                  70                  75                  80

His His Lys Lys Lys His His His His Lys Lys Lys His His His His
                85                  90                  95

Lys Lys Lys His His His His Lys Lys Lys His His His His Lys Lys
                100                 105                 110

Lys His His His His Lys Lys Lys His His His His Lys Lys Lys His
        115                 120                 125

His His His Lys Lys Lys His His His His Lys Lys Lys His His His
        130                 135                 140

His Lys Lys Lys His His His His Lys Lys Lys His His His His Lys
145                 150                 155                 160

Lys Lys His His His His Lys Lys Lys His His His His Lys Lys Lys
        165                 170                 175

His His His His Lys Lys Lys His His His His Lys Lys Lys His His
        180                 185                 190

His His Lys Lys Lys His His His His Lys Lys Lys His His His His
        195                 200                 205

Lys Lys Lys His His His His Lys Lys Lys His His His His Lys Lys
        210                 215                 220

Lys His His His His Lys Lys Lys His His His His Lys Lys Lys His
225                 230                 235                 240

His His His Lys Lys Lys His His His His Lys Lys Lys His His His
        245                 250                 255

His Lys Lys Lys His His His His Lys Lys Lys His His His His Lys
        260                 265                 270

Lys Lys His His His His Lys Lys Lys Cys
        275                 280

<210> SEQ ID NO 39
<211> LENGTH: 25
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(23)
<223> OTHER INFORMATION: 2', 2'-difluoro 2'-deoxycytidine

<400> SEQUENCE: 39
aagaaagaga ucuguaucaa ucctt                                          25

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
aagaaagaga ucuguaucaa utt                                            23

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(23)
<223> OTHER INFORMATION: 2', 2'-difluoro 2'-deoxycytidine

<400> SEQUENCE: 41
auugauacag aucucuuucu ucctt                                          25
```

OLIGONUCLEOTIDES WITH NUCLEOSIDE ANALOGS

RELATED APPLICATIONS

This application is a continuation of International Application No. PCT/US2020/54093, filed Oct. 2, 2020, claiming priority under 35 USC 119(e) to U.S. provisional applications 62/909,526, filed Oct. 2, 2019; 62/927,500, filed Oct. 29, 2019; and 62/977,630, filed Feb. 17, 2020, the contents of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 13, 2022, is named 4690_0015C_SL.txt and is 39,442 bytes in size.

BACKGROUND OF THE INVENTION

SiRNAs are double stranded RNA molecules consisting of a sense strand and a complementary antisense strand. These molecules may be blunt ended molecules that are 19-29 bases long on each strand or they may exhibit two base overhangs (typically dTdT).

Each strand of the siRNA typically is made on a synthesizer by conjugating the next base in the desired sequence to the previous base attached to the growing oligonucleotide. Amidite chemistry or other synthetic approaches are well known in the field. Once synthesized, the two strands are then annealed to each other to form the duplex.

It has been demonstrated that siRNAs against select targets within a cancer cell may be able to reduce expression of a protein encoded by the silenced gene target. Silencing these genes can, in turn, inhibit growth of that cell. If the cell is specifically a diseased cell (e.g. a cancer cell) that the siRNA can access, then the siRNA may act as a therapeutic. Furthermore, in some cases, it has been found that the use of select therapeutics (small molecule inhibitors, monoclonal antibodies, etc.) that are currently the 'gold standard' for therapy can be augmented by silencing genes in select pathways.

Gemcitabine (2',2'-difluoro 2'-deoxycytidine) is a pyrimidine based nucleoside analogue that, when administered systemically, is taken up by nucleoside transporters, activated by tri-phosphorylation by deoxycytidine kinase and can then be incorporated into either RNA or DNA. It replaces the nucleic acid cytidine during DNA replication (during cell division) and can inhibit tumor growth since new nucleosides cannot be attached to this nucleoside mimic resulting in apoptosis of the cells (Damaraju et al., *Oncogene* 22:7524-7536 (2003)).

Gemcitabine is the primary therapeutic in treating pancreatic cancer (Burris et al., *J Clin Oncol* 15:2403-2413 (1997) but is used in the treatment of a number of other cancers including cholangiocarcinoma (Jo and Song, "Chemotherapy of Cholangiocarcinoma: Current Management and Future Directions. Topics in the Surgery of the Biliary Tree", chapter 3; p 35-52. http://dx.doi.org/10.5772/intechopen.76134, S.Y. (2018)), non-small cell lung cancer (Muggia et al., *Expert Opinion on Investigational Drugs,* 21:4, 403-408 (2012)), ovarian cancer (Le et al., *Gynaecol. Oncol. Res. Pract.* 4:16 (2017) and breast cancer (Xie et al., *Oncotarget,* 9:7148-7161 (2018)). Gemcitabine is taken up by nucleoside transporters, is activated by deoxycytidine kinase, and is incorporated into both RNA and DNA. Inhibition of ribonucleotide reductase and dCMP deaminase enhances its activation, while cytidine deaminase converts gemcitabine to its presumably inactive metabolite 2',2'-difluorodeoxyuridine, which in its nucleotide form may inhibit thymidylate synthase. Gemcitabine is administered systemically by IV infusion into the patients. Standard administration of gemcitabine is with a 30-min weekly infusion at 1000 mg/m², but is limited in its utility since it exhibits significant toxicity due to its distribution not only to tumor cells but also into normal cells. Furthermore, to see efficacy in some tumor types, the dose needs to be elevated to very high levels, and the therapeutic index for the drug can be very limited.

Gemcitabine is widely used in combination, predominantly with a platinum analog. Other alternatives for combinations of gemcitabine in ovarian cancer consist of increasing the inhibition of ribonucleotide reductase with triapine or hydroxyurea.

Various ways to overcome gemcitabine toxicity have been tried. One of the most promising is the use of targeted delivery agents that selectively enrich delivery to the tumor cells while reducing its delivery to normal cells.

An example of genes that augment the action of the compound gemcitabine have included siRNAs targeting RAD17, CHK1, CHK2, ATR, ATM just to name a few (see: Azorsa, *J. Transl. Med.* 7:43 (2009); Fredebohm (*Journal of Cell Science* 126:3380-3389, 2013), and Plunkett et al., *Semin Oncol* 23:3-15 (1996)).

Studies as mentioned above have sought to find additional targets within the cell that, when inhibited (by antagonists such as small molecules or antibodies etc.) or silenced (using siRNA or miRNAs), results in a beneficial shift in the dose response curve for the drug to where it exhibits equal efficacy but at lower doses/concentrations.

Such a shift in dose response is seen with siRNAs against RAD17 or CHK1 (as examples).

Delivery of these siRNAs to the tumor environment within the animal/human exhibiting the disease can be accomplished using a variety of targeted or non-targeted delivery agents. These delivery vehicles can consist of lipids, modified lipids, peptide delivery vehicles and the like or can even be via direct attachment of a targeting ligand onto a modified (chemically stable) siRNA molecule through modification of the backbone to prevent degradation of the siRNA by nucleases and other enzymes encountered in the circulation.

Recently, GalNAc modified siRNAs have been used to promote delivery of these siRNAs specifically to hepatocytes within the liver. The GalNac moieties bind with very high affinity to the asialoglycoprotein receptors (ASGPR) present specifically and at high numbers on the hepatocytes. The ASGPRs are believed to be internalized into the cells upon binding and therefore carry the attached siRNA into the cell with them.

Other targeting ligands that can deliver a payload to specific cell types include the GLP1 peptide (binding to the GLP1 receptor on Pancreatic Beta cells), RGD motifs (e.g. cRGD, iRGD that bind α5β3 integrin receptors or peptides derived from the Foot and Mouth virus (binding with nM affinity to α5β6 integrin receptors compared with almost micromolar affinity for α5β3 receptors)), Folate ligands (that bind to folate receptors), Transferrin ligands binding to Transferrin receptors and EGFR targeting through EGF receptors. Many other examples of targeting moieties show specificity for delivery to distinct cell types.

Compositions and methods are described herein that provide co-delivery of an siRNA (that will silence a gene) along with a drug (e.g. gemcitabine) to produce a therapeutic benefit that is greater than administration of either the siRNA or the drug alone.

Gemcitabine (like 5-FU and other nucleoside analogs) can be chemically synthesized in a manner to allow direct coupling to DNA or RNA bases through traditional synthetic means (manually or using automated instruments).

BRIEF DESCRIPTION OF DRAWINGS

FIG. 1 shows the basic structure of the oligonucleotide sense strand sequence with polyGEM additions.

FIGS. 2(a) and (b) show the antisense oligonucleotide ("ASO") sequence and its delivery:

FIG. 2(a) shows the ASO sequence with a polyGEM tail; and

FIG. 2(b) shows the targeted ASO delivery via a targeting ligand.

FIGS. 3(a) and (b) show targeted oligonucleotide delivery:

FIG. 3(a) shows a targeting ligand attached to the sense strand; and

FIG. 3(b) shows a targeting ligand attached to the ASO strand.

FIG. 4 shows the polyGEM conjugated into a single oligonucleotide with both sense and antisense strands of equal length, forming a polyGEM loop.

FIG. 5 shows the conjugated single oligonucleotide having different lengths (partially conjugated) with the polyGEM loop.

FIG. 6 shows multiple ligands attached through linkers to the polyGEM loop region.

FIG. 7 shows that ligands may be attached with an asymmetric strand construct.

FIGS. 9(a) and (b) show sensitivity in pancreatic cancer cells of a number of siRNA sequences designed against CHK1 using BPC3 cells (a), and in CFPAC cells (b).

Figure 10:
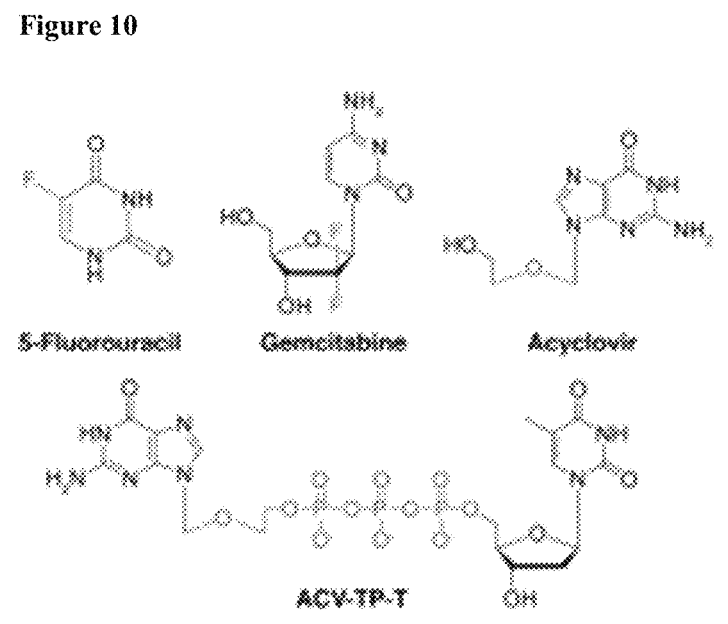

FIG. 10 shows the structures of 5'-fluorouricil, gemcitabine, acyclovir, and ACV-TP-T.

FIG. 12(a)-12(d) show the effects of adding two gemcitabine nucleotides at the 3' end of the sense strand of each CHK1 and RAD17 siRNA molecules on potency and efficacy in BxPC3 cells, evaluating:

FIG. 12(a): P49-2 (CHK1_de_2GEM), P49-4 (RAD17/2GEM); GEM; CHK-az-25; and CHK-az-poly2;

FIG. 12(b): P49-1 (CHK1_de); CHK-az; 2POlyG_az; P49-2 (CHK)de_2GEM; and GEM;

FIG. 12(c): P49-1 (CHK1_de), P49-7 (CHK1_de-full_4GEM); P49-4 (RAD17/2GEM); P49-2(CHK)de_2GEM; P49-3 (RAD17) and GEM; and FIG. 12(d): P49-A (CHK1_de); CHK1az; 2PolyG_az; P49-2 (CHK1_de_2GWM); CHK_az-25; and GEM.

Figure 8:
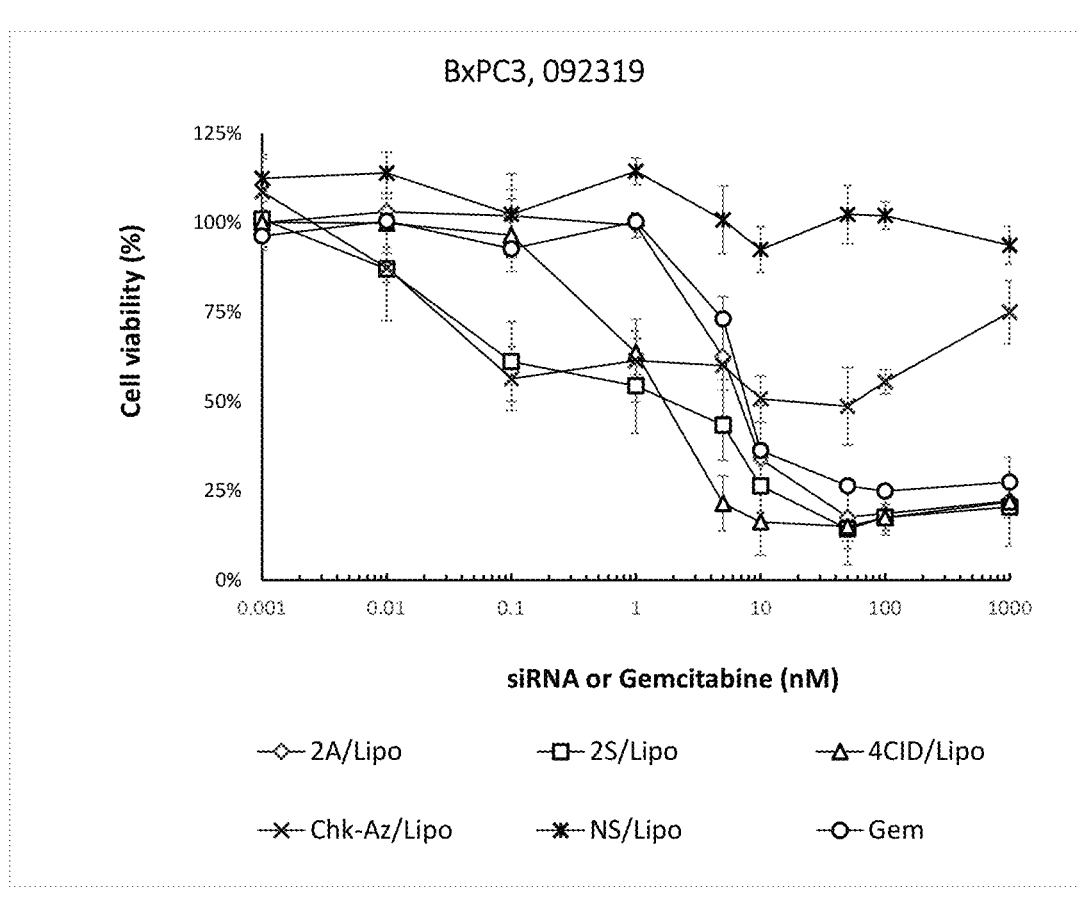
FIG. 8 shows cell viability (line graph) with a variety of sequences, including CHK1-AZ.

DETAILED DESCRIPTION siRNA compositions are provided that contain gemcitabine (GEM) in place of cytosine moieties within the siRNA sequence. Pharmaceuticals compositions containing these siRNA molecules, and methods of using the compositions for treating diseases such as cancer are provided.

Definitions

Small interfering RNA (siRNA): a duplex oligonucleotide that is a short, double-stranded RNA that interferes with the expression of a gene in a cell, after the molecule is introduced into the cell. For example, it targets and binds to a complementary nucleotide sequence in a single stranded target RNA molecule. SiRNA molecules are chemically synthesized or otherwise constructed by techniques known to those skilled in the art. Such techniques are described in U.S. Pat. Nos. 5,898,031, 6,107,094, 6,506,559, 7,056,704, RE46,873 E, and U.S. Pat. No. 9,642,873 B2 and in European Pat. Nos. 1214945 and 1230375, all of which are incorporated herein by reference in their entireties. By convention in the field, when an siRNA molecule is identified by a particular nucleotide sequence, the sequence refers to the sense strand of the duplex molecule. One or more of the ribonucleotides comprising the molecule can be chemically modified by techniques known in the art. In addition to being modified at the level of one or more of its individual nucleotides, the backbone of the oligonucleotide can be modified. Additional modifications include the use of small molecules (e.g. sugar molecules), amino acids, peptides, cholesterol, and other large molecules for conjugation onto the siRNA molecule.

MicroRNA (miRNA): a small, non-coding RNA molecule that functions in RNA silencing and post-transcriptional regulation of gene expression by targeting and binding to a complementary nucleotide sequence in a single-stranded target RNA molecule.

Anti-sense oligonucleotide (ASO): a short, single-stranded RNA or DNA (typically 11-27 bases) that can reduce expression of a gene within a mammalian cell by targeting and binding to a complementary nucleotide sequence in a single-stranded target RNA molecule.

A DNA or RNA aptamer: a single-stranded DNA or RNA oligonucleotide that binds to a specific target molecule. Such targets include small molecules, proteins, and nucleic acids. Such aptamers are usually created from a large random sequence pool through repeated rounds of in vitro selection or systematic evolution of ligands by exponential enrichment (SELEX).

PolyGEM sequence: a sequence comprising multiple gemcitabine nucleosides in a row.

OligoGEM: an oligonucleotide having multiple gemcitabine nucleosides. The nucleosides can be in a row at either end or within the oligonucleotide, or they can be interspersed within the oligonucleotide, including a single nucleoside at one or both ends.

Histidine-lysine copolymer: a peptide or polypeptide consisting of histidine and lysine amino acids. Such copolymers are described in U.S. Pat. Nos. 7,070,807 B2, 7,163,695 B2, and 7,772,201 B2, which are incorporated herein by reference in their entireties.

A cancer is any malignant tumor.

A malignant tumor is a mass of neoplastic cells.

Liver cancer: any primary cancer within the liver, i.e., one that starts in the liver; or any secondary cancer within the liver, i.e., a cancer that metastasizes to the liver from another tissue in the mammal's body. An example of a primary liver cancer is hepatocellular carcinoma. An example of a secondary liver cancer is a colon cancer.

Treating/treatment: killing some or all of the cancer cells, reducing the size of the cancer, inhibiting the growth of the cancer, or reducing the growth rate of the cancer.

Enhancing the antitumor efficacy: means providing a greater reduction in growth rate of the tumor cells, greater effect in killing the tumor cells and/or reducing tumor mass and eventually producing a better therapeutic effect by prolonging life of the patient with the tumor.

Target Selection for Augmentation of GEM Activity

Constructs Containing GEM

Azorsa et al. (J. Transl. Med. 7:43 (2009)) identified siRNAs against the gene CHK1 that showed a potentiation of the effect of gemcitabine in pancreatic cancer cells in culture. Subsequently, Fredebohm (Journal of Cell Science 126:3380-3389, 2013) validated CHK1 as a potentiator of the effect of gemcitabine in pancreatic tumor cells but also identified several other potential targets that improved the activity of gemcitabine when silenced. RAD17 was identified as one of these targets and demonstrated a profound improvement in the action of gemcitabine in reducing cell viability.

RAD17 was suggested as a better target than CHK1 since silencing this gene alone had almost no effect on cell viability but, when gemcitabine was included, the synergism in reducing cancer cell viability was also evident. However, CHK1 silencing itself was shown to exhibit some toxicity in cells—even without the presence of gemcitabine—and this would require that the use of an siRNA against CHK1 would need to be administered in a way to get preferential uptake into tumor cells and not into normal dividing cells.

It has been shown that RAD17 inhibition may also synergize with inhibition of checkpoint kinases (Shen et al., Oncotarget 6:35755-35769 (2015)). It may therefore be possible to co-deliver siRNAs against both targets—RAD17 and CHK1 to further augment activity against pancreatic cancer. As described herein, siRNAs against RAD17 and CHK1 may both be modified with gemcitabine nucleotides within the Sense Strand or appended to the end of the Sense Strand, and the 2 Gem-modified siRNAs can be combined in a single polypeptide nanoparticle that results in improved efficacy when transfected into cells. In addition, polypeptide nanoparticles ("PNP") prepared using a Histidine-Lysine branched copolymer can simultaneously deliver multiple siRNAs to the same cell concomitantly. These PNPs also can be used to deliver siRNAs to a wide array of tumor cell types when represented as xenografts in animal models.

As described below, siRNA molecules may be prepared that contain GEM moieties linked to the terminus of the siRNA sequence and/or internal within the sequence. These GEM-containing siRNAs remain functional to silence a target gene and produce enhanced efficacy in killing a tumor via release of GEM into the cell, where a synergistic effect is seen between the gene silencing activity and the effect of the drug, i.e. the result seen is greater than that achieved by administering the siRNA and GEM as separate components individually.

In order to determine whether GEMs would be better processed if separated by native nucleotides, we took advantage of the fact that gemcitabine is an analog of the nucleotide Cytidine and so could be incorporated directly into an siRNA sequence in place of the Cytidines (Cs). Gemcitabine amidite may be used to form polymers entirely consisting of GEM moieties. (Ma et al, Chem. Commun., 55:6603-6606 (2019)) These polymers formed nanogels and these demonstrated some activity in cancer cell models in vitro and in vivo. A modified nucleoside incorporating the amidite functional group may be used to introduce the modified nucleoside, such as GEM, into one of the chains in the duplex during their synthesis. Since the antisense strand from the siRNA duplex has to anneal with its appropriate sequence in the sense strand within the siRNA region, and the antisense strand is incorporated into the RISC complex and used to surveil for matching mRNA sequences, the modified nucleosides was first appended to the sense strand of the siRNA to form an extension in length of the sense strand relative to the antisense strand. Multiple (n) non-natural nucleoside bases can be incorporated at the termini of the strand such that delivery of a single siRNA molecule results in co-delivery of multiple (n) non-natural nucleosides.

Once inside the cell cytoplasm, the antisense strand is incorporated into the RISC complex and, if a matching mRNA sequence is identified, the mRNA is cleaved by the enzyme DICER. The SENSE strand is removed during this process and is then cleaved within the cytoplasm. Non-natural nucleoside analogs incorporated onto the ends of the Sense strand will then be cleaved off by endogenous nucleases. The freed molecules of gemcitabine (or similar structures with anti-cancer non-natural nucleoside analogs) then inhibit the tumor cell replication machinery and, in concert with the reduction in the gene expression targeted by the siRNA, will exhibit a better effect on reducing tumor cell growth than in the absence of these agents.

Chemically unmodified siRNA molecules that incorporate GEM residues can be delivered in a suitable nanoparticle formulation that protects the siRNA from degradation in circulation through the blood or in the tissue, tumor microenvironment etc. Once inside the tumor or tissue of interest, the siRNA is released into the tumor cells to produce its cytotoxic effect.

siRNA molecules synthesized using the GEM amidites can be delivered with a Histidine Lysine polypeptide nanoparticle (HKP PNP) nanoparticle system. GEMs can be included within an siRNA duplex sequence that targets a gene that then augments the action of the gemcitabine in killing the tumor cells—reducing the amount required for administration to observe a therapeutic effect and decreasing the potential for toxic effects observed when gemcitabine alone is administered in patients. As described below, a previously published siRNA sequence against CHK1 (Azorsa, supra) was selected that had demonstrated potentiation of gemcitabine action when gemcitabine was administered separately from the siRNA (i.e. as individual components).

The siRNAs can be stabilized against nuclease degradation by chemical modification, using methods that are well known in the art, e.g. by use of 2'-OMe and/or 2'-F and/or phosphorothioate modifications. The siRNA can optionally be chemically linked (via the terminus of the SS or AS or even via the terminal GEM added to the molecule) to a targeting moiety (e.g. GalNac, RGD, Folate, TFR, EGFR, peptide targeting ligands, aptamers or other carbohydrates or even small molecules or antibodies or nanobodies). The targeting moiety has affinity for a receptor or other target on the surface of the cells, which enriches uptake into these cells. As with unmodified siRNAs, the SS and AS strands will separate in the cell, the AS strand will result in silencing of the gene of interest while the released SS-polyGEM structure will be degraded, releasing GEM which, in combination with the silenced gene will exhibit greater effect than either alone.

The basic structure is shown in FIG. 1. FIG. 2 shows the antisense oligonucleotide ("ASO") sequence with a poly-GEM tail. FIG. 2b shows targeted ASO delivery via a targeting ligand. FIG. 3 shows targeted oligo delivery: FIG. 3a shows a targeting ligand attached to the Sense strand, while FIG. 3b shows a targeting ligand attached to the Antisense strand Poly gemcitabine can also be conjugated into a single oligonucleotide, having both sense strand and antisense strands of equal length (see FIG. 4). After annealing it forms a "poly gemcitabine loop" connected between the two strands of a double stranded RNA. A single oligonucleotide sequence has a reduced cost of manufacture compared to two strands and also has the potential to have improved stability of the product and the ability to deliver a much larger number of GEM molecules per siRNA delivered into a cell, thereby improving efficacy against the cancer cell. Furthermore, in certain circumstances it may not be necessary for the two strands of the RNA to be of the same length provided there are enough bases in the shorter strand to allow hybridization with the relevant cognate sequence in the longer strand (see FIG. 5). Under these circumstances the gemcitabine loop may not be symmetrical between the 2 strands.

In another embodiment these constructs are targeted for delivery to specific cell types by attaching a targeting ligand that binds with high affinity to a target present at higher levels on the target cells than on other, non-target, cells. For targeted delivery, multiple ligands can be attached to the gemcitabine loop region (see FIG. 6)—providing the advantage of multivalent targeting by multiple ligands binding to their targets at the same time (increasing avidity of binding and possibly improving cell specificity). The targeting ligands are conjugated with the gemcitabine at the loop region through linkers. This allows delivery of the oligo and gemcitabine conjugates specifically to the targeted cell or tissue, where they can then induce an additive or synergistic or broader therapeutic effect. Ligands may also be added to the Gem loop in the asymmetric strand construct (FIG. 7).

Specific examples of CHK1 siRNA molecules containing GEM moieties are shown below. The SS and AS strands, in the absence of the GEMs, anneal to form an siRNA targeting CHK1. This specific sequence was designed to have identity between human and mouse CHK1 genes and, as described below, was shown to be more potent in silencing the gene than the CHK1_AZ sequence (see FIGS. 8 and 9.

8

```
([GEM] in place of "C")
                                        (SEQ ID NO: 1)
SS = 5'-CCU GUG GAA UAG UA[GEM] UUA [GEM]UG

[GEM]AA U-3'

(No GEMS on AS strand)
                                        (SEQ ID NO: 2)
AS = 5'-A UUG CAG UAA GUA CUA UUC CAC AGG-3'
```

In other molecules, additional GEMs were attached at the end of SS:

```
([GEM] in place of "C" AND GEM added to
3' end)
                                        (SEQ ID NO: 3)
SS = 5'-CCU GUG GAA UAG UA[GEM] UUA [GEM]UG-

[GEM]AA U[GEM][GEM]....[GEM} 3'

(No GEMS on AS strand)
                                        (SEQ ID NO: 2)
AS = 5'-A UUG CAGUAA GUA CUA UUC CAC AGG-3'
```

Since gemcitabine is a Cytidine analog, it may be used to replace the cytidine moieties in an RNA oligonucleotide sequence with the gemcitabine moieties or the deoxycytidine moieties in a DNA oligonucleotide. These GEMs will still hybridize with their counterparts on a second strand of an oligonucleotide i.e. GEM will hybridize with a "G" (guanosine/deoxyguanosine) on the opposite strand. Accordingly, the siRNA sequence targeting a gene that, when silenced, produces inhibition of cell growth and can kill tumor cells, is augmented by inclusion of GEM moieties in place of the cytosine moieties in either the Sense Strand or the Antisense strand of an siRNA or an miRNA or even in a single stranded sequence like for an antisense oligonucleotide (ASO). As described below, replacing two cytosine moieties with GEMs in the CHK1_AZ sequence for siRNA silencing the CHK1 gene augments the inhibitory activity of the siRNA alone (see experiments below).

```
([GEM] in place of "C")
                                        (SEQ ID NO: 1)
SS = 5'-CCU GUG GAA UAG UA[GEM] UUA [GEM]UG

[GEM]AA U-3'

(No GEMS on AS strand)
                                        (SEQ ID NO: 2)
AS = 5'-A UUG CAGUAA GUA CUA UUC CAC AGG-3'
```

GEM additions can also be on the 3' or 5' end of the Sense strand. They also can be added to the same on the AS strand. The additions independently can contain 1, 2, 3, 4, or more GEM moieties.

Other nucleoside anticancer agents can be attached to the oligonucleotide backbone in place of gemcitabine. Such analogs may include Cytarabine (ara-C), 5-FU, 5-Deoxy-5-fluorouridine, Fludarabine, Capecitabine, Cladribine, Troxacitabine or Clofarabine, Azacytidine and 5-deoxy Azacytidine to name just a few examples (see Damaraju, supra).

A number of siRNA sequences can be attached to the polynucleoside analog chains on the sense strand or antisense strand. Examples of such siRNA sequences are siRNAs that silence genes encoding proteins that are counterproductive to the inhibitory mechanism of the nucleoside analogs. For example, an siRNA can be used to silence the enzymes responsible for deamination and inactivation of gemcitabine (Cytidine deaminase or 5'-nucleotidase) or those responsible for enhanced release of the nucleoside from the cell—e.g. nucleoside transporters (see Damaraju supra and references therein].

Other potential targets that could be used as the siRNA sequence in these constructs (attached to Nucleoside analog chains) would include Multidrug resistance (MDR) proteins such as P-glycoprotein (P-gp) and multidrug resistance-associated protein-1 (MRP1), encoded by the MDR1 and MRP1 genes, respectively. Expression of these proteins confers a resistant phenotype to a broad spectrum of drugs used in cancer chemotherapy. These transporters are broadly classified as ATP-binding cassette proteins (ABC) and constitute a superfamily of proteins. Silencing of the MDR1 and MRP1 genes using siRNA has been described. See Dönmez and Gündüz, *Biomed Pharmacother.* 65(2):85-9 (2011). Other examples of genes that can be silenced include methyl transferases, organic anion and cation transporters (OAT and OCT), oxidoreductase flavoproteins and Nucleoside Transporters (NTs), all of which are involved in drug transport and metabolism in cells and may impart drug resistance phenotypes to cancer cells.

Other gene targets for the siRNAs are those that have been validated to augment the action of gemcitabine or the other nucleoside analogs when silenced themselves. Such gene targets include ATR and WEE1, in addition to CHK1, RAD17. As other targets are silenced and demonstrated to augment nucleoside activity, these can also have siRNAs against them coupled to the appropriate nucleoside analog.

In using the Azorsa sequence there were 2 Cs that could be replaced on the SS and on the AS strands respectively. We therefore made a construct where just the SS was modified with incorporation of 2 Gems in place of Cs and we made the AS strand in the same way. We then annealed the SS containing 2 GEMs with an unmodified AS strand and we annealed a GEM-modified AS strand with an unmodified SS. We further annealed the GEM modified SS with the GEM modified AS strand. All of these constructs were compared with the siRNA where neither strand was modified and with the dose response of gemcitabine alone.

The siRNA sequence identified by Azorsa et al. (CHK1_AZ) is an example of an siRNA that can be used to prepare molecules containing GEM moieties. Using an oligonucleotide synthesizer, the following siRNA strands were manufactured with and without GEM residues included in place of the natural cytidine ("C") groups present in the sequence.

C1D-2A—(sequence AUUGAUACAGAUCUC-UUUCUU (SEQ ID NO: 4)) refers to the CHK1 siRNA ANTISENSE strand containing 2 GEM residues in place of cytidine residues, and has dTdT at 3' end; this is annealed with the SENSE strand (SS) (sequence AAGAAAGAGAUCUGUAUCAAU (SEQ ID NO: 5)) that does NOT contain any GEMs.

C1D-2S—refers to the CHK1 siRNA SENSE strand that contains 2 GEM residues in place of cytidines and has dTdT at 3' end; this is annealed with the ANTISENSE strand (AS) that does NOT contain any GEMs C1D-4—refers to the CHK1 siRNA ANTISENSE strand that contains 2 GEM residues that is annealed with the SENSE strand (SS) that ALSO contains 2 GEMs—i.e. 4 gems per siRNA. Both strands have dTdT at 3' end as above.

Analogs of this siRNA were synthesized where 2, 4 or 6 GEMs were appended on the 3' end of the SS and also designed several different siRNAs where the Cs within the sequence could be modified by inserting GEM in their place. GEMs were inserted in place of Cs within the Sense Strand and in the Antisense Strand separately or in combination to explore whether increasing GEM content improved efficacy or potency. Unmodified CHK1 siRNA, C1D-2A, C1D-2S and C1D-4 were transfected into the pancreatic cancer cell line BxPC3 that has been shown to be sensitive to CHK1+Gem (Azorsa, supra). A dose response of gemcitabine alone was carried out, together with transfection of non-silencing siRNA (as a control).

It was observed that appending additional GEMs to the 3' end of the SS (ahead of the usual dTdT end groups) had no additive effect greater than adding 2 GEMs and there was no increase in potency and efficacy when 4 or 6 were added. Without being bound by theory, it was suspected that the nucleases present within a cell are unable to cleave the polyGEM sequences between the GEM moieties but can only cleave a GEM from its prior unmodified nucleotide—releasing just 1 GEM from within the polyGEM sequences irrespective of the number of GEMs in the sequence. Consequently, constructs with 4 or 6 GEMs at the 3' end of the SS had equal or slightly worse potency when compared with 2GEMs at this location.

Insertion of GEMs in place of Cs in the SS resulted in a product with improved $IC_{50}$ and efficacy ($IC_{50}$=0.38 nM (FIG. 6)) compared with unmodified siRNA incubated for the same time ($IC_{50}$=3 nM; FIG. 5 right panel)). Adding GEMs in to the Antisense strand in place of C residues had the potential to interfere with the loading of the siRNA into the RISC complex or the subsequent recognition of the cognate mRNA and subsequent cleavage by Dicer. However, with the specific CHK1 siRNA sequence selected it was found that adding GEMs in to the AS strand improved potency and efficacy ($IC_{50}$ 1.8 nM) but not to the extent observed for the SS. Furthermore, combining the 2 strands (now containing 4 GEMs total) did not provide a further improvement in potency (1.98 nM) that might be expected if the principal contribution was from release of GEMs from both strands. This $IC_{50}$ was similar to that with the 2GEMs in the AS strand alone. It is known that, during loading of the siRNA into the RISC complex, the strands are separated and the Sense strand is released into the cytoplasm where it is degraded. The AS strand is retained in RISC for some time and hence may not contribute GEMs to the mixture—so all GEMs come from the SS.

This was also confirmed in QPCR analysis of the silencing induced by the various constructs. FIG. 4 shows that equivalent gene silencing by the siRNAs was obtained, irrespective of the number of GEMs on the SS, the AS strand or both strands.

When an siRNA is processed within the cell, the antisense strand is unwound from the Sense strand and loaded into the RISC complex where it surveils the cell for the cognate mRNA sequence. Once identified and bound by the antisense strand, the mRNA is cleaved by the enzyme DICER antisense strand is loaded into RISC, the sense strand is released into the cytoplasm where it is degraded. In previous publications (Ma et al., 2019), polygemcitabine nanogels consisting of recurring sequences of 10 gemcitabines were synthesized and these structures self-annealed to form nanogels that then showed improved efficacy in pancreatic tumor cells. Addition of a recurring sequence of GEMs on the ends of the sense strand was expected to produce similar improvement in delivery of gemcitabine at the same time the siRNA was delivered into the cell. However, it was found that addition of either 2, 4 or 6 Gems on the [3'] end of the sense strand prior to annealing with an unmodified antisense strand did not produce the expected increase in potency. Rather, the 2, 4 and 6 GEM sequences showed only the same potency as if 1 GEM was released from each sequence. This may be as a result of exo- or endonucleases not being able to cleave the polyGEM sequences or it may be as a result of very slow release and subsequent phosphorylation to activate the gems. Results of efficacy of each of these structures in cell viability experiments showed no improvement with increased incubation time (from 72 h to 96 h).

SiRNA Synthesis with GEM

The CHK-Az siRNAs were 19-mer siRNAs containing a 2 base (dTdT) overhang on the 3' end of each strand. When modified with the inclusion of the gemcitabine moieties within the Sense strand, we inserted these between the end of the sense strand and before the dTdT end groups. The dTdT ends may help stabilize the siRNA sequences against nuclease degradation and this, in turn, may affect the rate of release of the Gems from the Sense strand when it is separated from the AS in the RISC complex during surveillance of the AS strand for the cognate mRNA sequence to be cleaved and silenced.

Rationale for Improvement in CHK1_AZ with GEMs Compared with 25mer with GEMs.

The 25mer siRNAs we designed were blunt ended siRNAs whereas the siRNA sequence used by Azorsa was a 19mer siRNA with a 2 base (dTdT) overhang at the 3' end. When 2 GEM moieties were added between the last nucleotide in the siRNA SS and the dTdT overhang we saw that this sequence showed much higher efficacy against MiaPaca cells than BxPC3 cells. The inclusion of the dTdT on the end of the sequence may decrease the rate of release of the GEMs from the SS in this construct when the SS is unwound from the AS strand and released into the cytoplasm. This may allow the AS sequence to induce silencing of the gene before the GEMs are released from the SS and this may augment the efficacy of this combination in MiaPaca cells compared with BxPC3 cells.

Improved Options for Pancreatic Cancer Therapy

From the data presented it would appear that we can demonstrate a dramatic improvement in the efficacy of gemcitabine action in pancreatic cancer cells by including gemcitabine. Incorporation of multiple GEMs into the sense strand of an siRNA can deliver GEMs to the same cell where the siRNA is having its effect. In previous studies (Azorsa, 2009) it was shown that silencing CHK1 could augment the action of gemcitabine. Therefore adding GEMs to the siRNA sequence able to silence CHK1 we would expect some additivity/synergy in the interactions. Using a Histidine Lysine polypeptide nanoparticle (PNP) we have demonstrated the ability to deliver siRNAs to many different tumor types in vitro and in vivo. We therefore are studying the delivery of the GEM CHK1 siRNAs as a new therapeutic modality to treat cancer. Furthermore, the polypeptide nanoparticle is able to deliver siRNAs against more than one target to the same cell at the same time so we can also silence a second gene target that can synergize with the first siRNA. A publication (Paul et al., 2015) demonstrated synergy between CHK1 and RAD17 inhibition in pancreatic cancer and therefore it is feasible that we can benefit from silencing RAD17 in combination with the GEM-CHK1 siRNA. If the amount of gemcitabine delivered by the GEM-Chk1 siRNA is insufficient to produce a robust effect in vitro and/or in vivo then we can further modify RAD17 SS to introduce Gems in this sequence in place of the "C"s.

Gemcitabine Options

Gemcitabine activity can be augmented by inhibition of ribonucleotide reductase and dCMP deaminase.

Gemcitabine is widely used in combination, predominantly with a platinum analog, with other combinations less frequently used or currently being explored. Standard administration of gemcitabine is with a 30-min weekly infusion at 1000 mg/m2, but alternatives are being explored such as prodrugs (e.g., CO-1.01, which can bypass transport deficiency), the fixed-dose rate infusion (10 mg/m2/min), and local routes of administration by a 24-h hepatic artery infusion, by instillation in the bladder or by intraperitoneal administration to treat advanced ovarian cancer. Other alternatives for combinations of gemcitabine in ovarian cancer consist of increasing the inhibition of ribonucleotide reductase with triapine or hydroxyurea. Gemcitabine's action on signaling also provides a rational concept for combination with signal transduction pathways.

Conclusion

Gemcitabine as an amidite can be included during synthesis of oligonucleotides and incorporates into the nucleotide sequence. We have demonstrated that addition of GEMs to an siRNA can allow co-delivery of the siRNA and the gemcitabine to the same cell. By selecting an siRNA against a molecular target that is expected to improve the effect of gemcitabine in reducing the viability of tumor cells we can see pronounced improvements in efficacy not seen with either agent alone.

While we elected to use siRNAs targeting CHK1 and RAD17 as examples the gemcitabines could be incorporated into any other oligonucleotides with similar results. Examples of siRNAs that augment gemcitabine activity have also described cMyc as a suitable gene target (Zhang et al., *Cancer Metastasis Rev* 26:85-110 (2013)). So an siRNA against cMyc could also have GEM incorporated directly and used to treat cancer, e.g. NSCLC. In fact, the oligonucleotides may not need to have a silencing effect at all, but can just be used to deliver the gemcitabines for efficacy against disease.

It is well known that chemical modifications to the bases within an oligonucleotide siRNA structure (e.g. 2'-OMe, 2'-Fluoro, phosphorothioate modifications etc.) can stabilize the oligonucleotide against nuclease attack when administered in vivo. It is feasible that such a chemically modified oligo could be directly coupled to a targeting ligand that would allow direct delivery through binding to a receptor on a cancer cell.

Additionally, antisense oligonucleotides have been used to alter expression of select genes within a cell and these single chain oligos may also be modified by gems. These modifications (at C bases) or additions to the terminus of the sequence may be used to assist in altering the hybridization efficiency to a specific target as well as for co-delivery of gemcitabines.

Similarly, miRNAs (mimics or inhibitors) have been described that have anti-cancer effects and these could be modified by insertion of gemcitabines in their sequences for do-delivery to the same cell. Especially miRNAs that can augment the action of gemcitabine would be of interest.

Finally, aptamers are RNA or DNA oligonucleotides that can be designed and made to bind with high affinity to select targets. In some instances these can be receptors on cells, or specifically receptors that are upregulated on cancer cells. Gem nucleotides can be appended or inserted into these sequences (in place of Cs) to allow high affinity binding to a target receptor on the cancer cell surface that then allows uptake of the oligo into the cell where the gemcitabine is released to exert a therapeutic effect.

Gemcitabine modified oligonucleotides (DNA or RNA) may have utility in improving cancer treatment options in multiple cancer types.

Gemcitabine is also able to act as a radiosensitizer (improving efficacy of radiation treatment of tumors). It is therefore feasible that gemcitabine would be delivered through the modification of oligos described above to specific cancer cells. Once the gemcitabine has been delivered, the tumor is exposed to radiation which then kills the tumor cells. Sometimes this radiation exposure can further produce an immune reaction against tumor specific antigens released in the process.

So oligonucleotides containing gemcitabine or other non-nucleoside analogs can be viable treatment modalities for cancer and other diseases where non-nucleoside (or nucleotide) analogs can be effective. Another example of the use of non-nucleoside analogs or nucleotide analogs is in the treatment of viral diseases. For example, in viral diseases it may be possible to co-administer an oligonucleotide containing a non-nucleoside (or nucleotide) analog. These may include the nucleoside and nucleotide reverse transcriptase inhibitors (NRTIs) such as zidovudine, didanosine, zalcitabine, stavudine, lamivudine, abacavir, emtricitabine and tenofovir or the non-nucleoside reverse transcriptase inhibitors (NNRTIs) such as nevirapine, delavirdine, efavirenz and etravirine.

EXAMPLES

Example 1

Methods

BxPC3 cells were seeded in two 384-well plates at 500 cells/well. On the next day cells were treated with various concentrations of CID2A, CID2S, CID4 siRNAs (formulated with Lipofectamine RNAiMAX) or gemcitabine (0.1-1000 nM) for 72 hrs. After incubation at 37° C. for 72 hrs, the number of viable cells was assessed using CTG2 reagent. Non-treated cells were set as 100%.
siRNA Design SiRNA against the Azorsa chk1 sequence was taken from the paper (Azorsa, supra). This is a 19mer with 2 dTdT base overhangs at the 3' end of each strand. To examine the ability to silence RAD17 and CHK1 using additional siRNAs, 25mer blunt ended siRNA sequences were designed that had identity between the genes for mouse and human.
siRNA Validation of Target Silencing (qRTPCR)

Data shows the relative effects of several siRNA designed against either RAD17 or CHK1 on their ability to silencing their respective target gene. These experiments were performed using the siRNAs shown below. The degree of gene target silencing was measured in cells transfected with the siRNAs at (50 nM) and the degree of gene silencing was measured using qRTPCR (using Beta-actin as a control housekeeping gene for normalization of the data).
Results FIG. 8 shows that the pancreatic cancer cell line BxPC3 shows no response to a Non-silencing siRNA (NS/lipo) administered using Lipofectamine as a delivery agent. However, when CHK1 siRNA was administered (Chk_Az/Lipo) using the same reagent, a reduction in cell viability was observed after 72 h exposure to about 50% as the dose increases. An siRNA oligonucleotide was manufactured where 2 Cytosines were replaced by GEMs in the Sense Strand of the CHK_Az siRNA sequence (2S/lipo) or 2 Cytosines were replaced by GEMs in the Antisense strand (2A/lipo). The GEM containing Sense strand was annealed with an unlabeled Antisense strand—to form 2S or the GEM containing ANTISense strand was annealed with an unlabeled Sense strand—to form 2A or the Sense strand containing 2 GEMs was annealed with the Antisense strand containing 2 GEMS to form compound 4. In the sequences selected, silencing activity was seen only for the CHK1 gene in the 2S product. Activity representing the gemcitabines was observed only in the 2A product. Furthermore, when GEM-SS was annealed with GEM-AS to get cpd4, no silencing effect for the siRNA sequence was seen, but a leftward shift in the dose response was observed due to the presence of 4 GEMs per siRNA. The graph in FIG. 8 shows the data presented in the table below the graph. The table represents the % of viable cells present under each treatment at the concentration indicated across the top row of the table (nM).

Results from this study confirm that GEMs can be added within the SS of an siRNA and augment activity of the siRNA silencing on killing tumor cells—specifically this pancreatic tumor line BxPC3. See FIG. 8

Non-silencing siRNA (NS) showed no effect on cell viability over the 72 h incubation period. Gemcitabine exposure (no Lipofectamine-gem) showed a dose dependent reduction in cell viability with an IC50 ~7 nM. Unmodified CHK1 siRNA (Chk-Az) showed a dose dependent effect up to 0.1 nM but then the effect plateaued at a maximum inhibition of 50% of cell viability.

Effect of Internal GEMs on Efficacy of CHK1 siRNAs

If 2 GEMs were included on the AS strand (2A) then the dose response looked very similar to the GEM alone dose response curve. If 2 GEMs were included on the SS (2S) then the initial part of the dose response curve looked more like the silencing produced by the CHK1 siRNA (0-0.1 nM). However, unlike the CHK1 siRNA effect that plateaus at 50% cell viability, 2S at concentrations above 1 nM continued to produce an inhibitory effect on cell viability, maxing out at 14% cell viability at 50 nM. This effect looked more like the response seen with GEM alone (maxing out at 26% cell viability at the same concentration (50 nM)). Annealing of the two strands that each contained 2 GEMs provided 4 GEMs per siRNA molecule (C1D-4). Compared to 2A a leftward shift in the dose response was seen for this material (reflecting the higher number of GEMs increasing potency). However, compared to CHK1 siRNA alone no initial reduction in cell viability was seen, but the curve paralleled that of GEM alone, suggesting the only effect was produced by introducing TWICE as many GEMs per siRNA.

Screening Identifies siRNA Sequences with Potency Against Pancreatic Tumor Cell Inhibition FIG. 9 shows the sensitivity of pancreatic cancer cell line viability upon transfection of a number of 8 siRNA sequences designed against CHK1. The percentage of viable cells 72 h after transfection of the siRNA sequences into cells in culture is shown (top panel—BxPC3 cells; lower panel—CFPAC cells). 100% viability is defined as that in the presence of a NON-silencing control siRNA (NS). CHK1_AZ (AZ) was tested as a comparator. CD=Cell Death siRNAs—known to produce maximal killing of many cell types when transfected into cells.

The Chk4 sequence provided the most potent effect in BxPC3 cells. It also had a very pronounced effect on cell viability when transfected into another pancreatic cancer cell—CFPAC.

The sequences tested were:

```
1.
                               (SEQ ID NO: 6)
GGGAGAAGGTGCCTATGGAGAAGTT 2.
                               (SEQ ID NO: 7)
GGAGAAGTTCAACTTGCTGTGAATA 3.
                               (SEQ ID NO: 8)
CCAGTTGATGTTTGGTCCTGTGGAA 4.
                               (SEQ ID NO: 9)
CCTGTGGAATAGTACTTACTGCAAT 5.
                              (SEQ ID NO: 10)
GGAATAACTCACAGGGATA 6.
                              (SEQ ID NO: 11)
GGGATATTAAACCAGAAAA 7.
                              (SEQ ID NO: 12)
GCAGAACCAGTTGATGTTT 8.
                              (SEQ ID NO: 13)
GGAATAGTACTTACTGCAA
```

Chk4 showed greater potency than CHK-AZ (The CHK1 siRNA sequence from the Azorsa paper) in BxPC3 cells. Furthermore, this sequence has 3 Cytosines where GEMs can be replaced compared with 2 on CHK1_AZ. This provides the possibility of greater potency in silencing the CHK1 gene, by delivering a larger number of GEMs per molecule, and further augments this activity and improves potency and efficacy compared with modified CHK1_AZ.

These data showed that:

1. Putting 2 GEMs on the SS of a CHK1 siRNA improves the efficacy compared with the siRNA alone.
2. Putting 2 GEMs on the AS strand—we do not see the effect of the siRNA silencing effect but we do see the effect of the GEMs on cell viability
3. Annealing the AS and SS—each containing 2 GEMs results in 4 GEMs per molecule. However, like #2, 2 GEMs on the AS strand prevents the AS strand from producing the gene silencing effect and we only see an improved potency since we are delivering 4 GEMs per siRNA.
4. The addition of the dTdT moieties on the 3' ends of each strand may slow release of GEMs allowing the discrimination of the effect away from the gene silencing effect
5. GEMs within the AS strand can inhibit the siRNA efficacy if they disrupt the ability for the AS strand to bind to the RISC complex and induce silencing of the targeted gene. However, GEMs on the 3' end of the AS strand have been demonstrated to show additive activity with the silencing induced by the AS strand. 1 or 2 GEMs may be added for this additive activity. Additional GEMs may be also be added.
6. GEMs on the SS improves efficacy by showing siRNA mediated silencing added with the inhibitory effect of GEMs on cell viability.

Combining this SS strand with 2×GEMs and an AS strand with 2×GEMs produces a better efficacy due to the 4 GEMs but there is NO silencing of the targeted gene by the siRNA.

Improved CHK1 siRNA (CHK_DE4) showed better silencing than the Azorsa sequence in previous studies The sequences tested were as follows: (These represent the Sense Strand sequences) CHK_X

| | | % viable BxPC3 cells at 72 h |
|---|---|---|
| 1. | GGGAGAAGGTGCCTATGGAGAAGTT (SEQ ID NO: 6) | 58% |
| 2. | GGAGAAGTTCAACTTGCTGTGAATA (SEQ ID NO: 7) | 28% |
| 3. | CCAGTTGATGTTTGGTCCTGTGGAA (SEQ ID NO: 8) | 31% |
| 4. | CCTGTGGAATAGTACTTACTGCAAT (SEQ ID NO: 9) | 24% |
| 5. | GGAATAACTCACAGGGATA (SEQ ID NO: 10) | 54% |
| 6. | GGGATATTAAACCAGAAAA (SEQ ID NO: 11) | 56% |
| 7. | GCAGAACCAGTTGATGTTT (SEQ ID NO: 12) | 64% |
| 8. | GGAATAGTACTTACTGCAA (SEQ ID NO: 13) | 76% |

```
#4 sequence CCTGTGGAATAGTACTTACTGCAAT (SEQ ID NO: 9) seemed to
be the best.

Therefore SS =
([GEM] in place of "C")
                               (SEQ ID NO: 1)
SS = 5'-CCU GUG GAA UAG UA[GEM] UUA [GEM]UG

[GEM]AA U-3'

(No GEMS on AS strand)
                               (SEQ ID NO: 2)
AS = 5'-A UUG CAGUAA GUA CUA UUC CAC AGG-3'
```

Make AS as all modified bases. Make SS as all modified (2'-O-Me) and make all as unmodified for comparison.

Additional sequences of interest:

```
CHK1A: target sequence:
CHK1-A:
                               (SEQ ID NO: 5)
AAGAAAGAGAUCUGUAUCAAU;

2 places for GEMs in place of "C"s

CHK1B: target sequence:
Chk1-B:
                              (SEQ ID NO: 14)
UUGGAAUAACUCCACGGGAUA
```

There are 4 places to put GEMs in this sequence.

We expect CHK1-B_AZ WITH 4 GEMs SS to show better activity than 2 in CHK1A.

Gemcitabine is used to treat a number of cancers, including bladder, pancreas, ovary, breast and non-small cell lung cancer. These other cancer types can be treated using the methods described herein, optionally using additional siRNA molecules to enhance the activity.

Example 2

Figure 11:
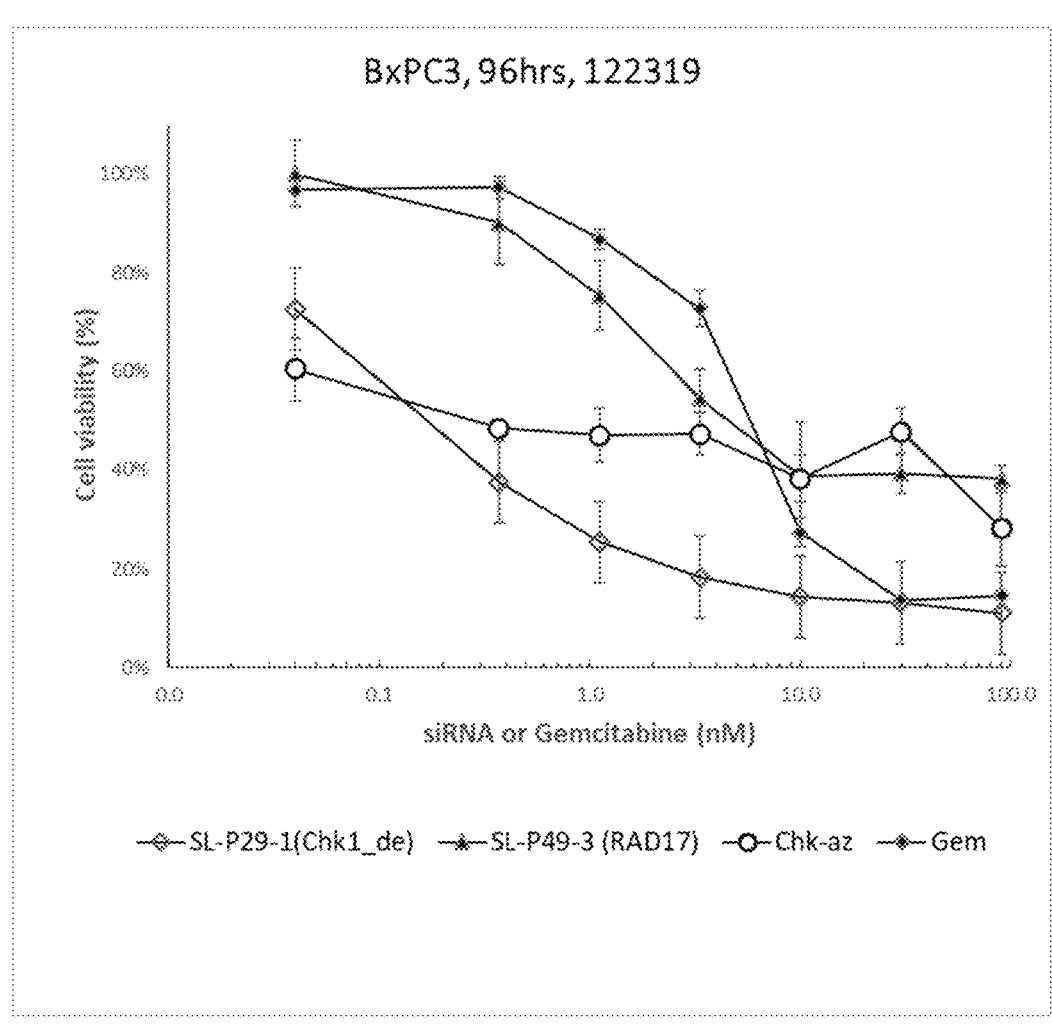
FIG. 11 shows pancreatic cancer cell (BxPC3) viability with CHK1 siRNAs.

Pancreatic cancer BxPC3 cells were seeded at 1000 cells/ml and grown as monolayers in 384 well plates. The cells were transfected with the siRNAs indicated against CHK1 or Rad17 using Lipofectamine (ThermoFisher) or were treated with gemcitabine at the concentrations indicated on the X axis. After a 96 h incubation at 37° C. with 5% $CO_2$, cell viability was determined using Cell Titer Glo (Perkin Elmer) by monitoring the luminescence signal produced by the reagent in a Perkin Elmer Envision plate reader equipped with Ultrasensitive luminescence detection optics. From the figure we can see that gemcitabine (GEM) produces a dose-dependent inhibition of cell viability with an IC50 of ~6 nM and maximal efficacy of >80% cell killing. A 25mer blunt ended siRNA against RAD17 produced a dose dependent inhibition in cell viability with a maximum efficacy at only 60% reduction in cell viability and an IC50 of ~5 nM. Using the previously published 19mer siRNA sequence against CHK1 from Azorsa, supra, we observed a similar maximal efficacy in cell viability similar to the Rad17 siRNA. A blunt ended 25mer siRNA against CHK1 showed a greater efficacy than the Azorsa CHK1 siRNA sequence with ~90% inhibition of cell viability at 100 nM. The IC50 for the latter siRNA was similar to that for the Azorsa sequence (~0.3 nM). The results shown in FIG. 11 demonstrate that SiRNAs against CHK1 and RAD17 alone can inhibit pancreatic cancer cell viability.

Example 3

SiRNAs were synthesized with gemcitabine nucleotide amidites added at the 3' end of each of the Sense strands for the siRNA sequences indicated. SiRNAs were transfected into the cells and incubated as detailed in FIG. 1. Maximal efficacy of all sequences was now improved to >95% inhibition of cell viability at concentrations above 10 nM. At very low concentrations (0.1 nM), the gemcitabine modified RAD17 siRNA itself had no effect on cell viability while the gemcitabine modified CHK1 siRNAs at this same concentration produced a 31% inhibition (25mer) or 56% inhibition (19mer) in cell viability. The gemcitabine nucleotides was examined to see if it could replace the Cytidine nucleotides within the siRNA sequence. The AZ CHk1 sequence had 2 "C" groups that were replaced by GEMs and we can see that this siRNA (CHK1-AZ-2S) behaved almost identically with the siRNA having 2 GEMs on the 3' end (CHK-AZ-Poly2). FIGS. 12a-12d show the effect of adding 2 gemcitabine nucleotides at the 3' end of the Sense strand of each siRNA on potency and efficacy.

Example 4

Figure 13:
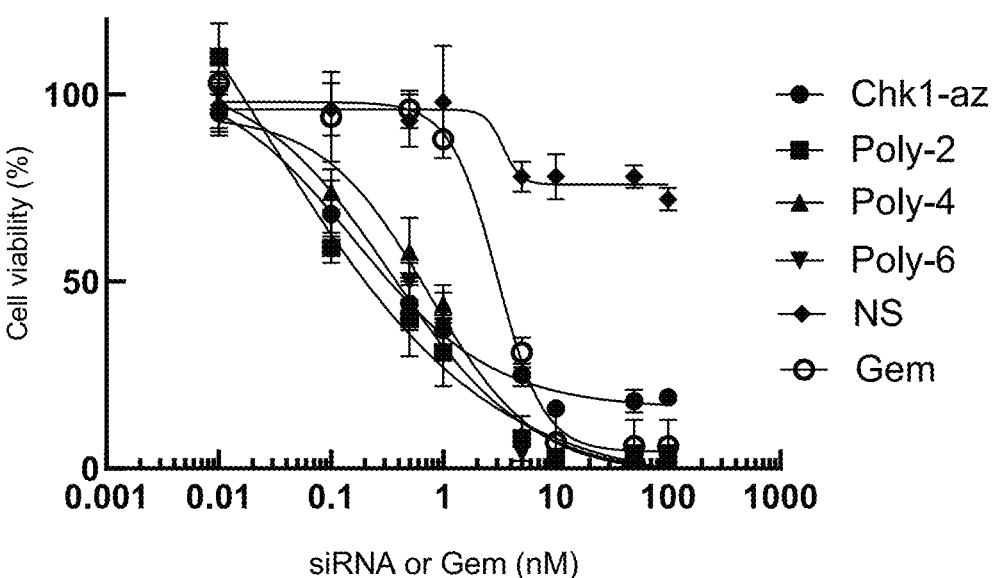
FIG. 13 shows cell viability in BxPC3 cells for CHK1-az; Poly[GEM]-2; Poly-4; Poly-6; GEM and non-silencing RNA (NS).

BxPC3 cells seeded in 384 well plates at 1000 cells/well were transfected with siRNA constructs or exposed to gemcitabine at the concentrations indicated in the figure. The samples tested were gemcitabine alone (GEM), the unmodified 19mer siRNA against CHK1 (CHK-AZ) and the same sequences of the siRNA but with either 2 (poly-2), 4 (poly-4) or 6 (poly-6) gemcitabine nucleotides added at the 3' end of the Sense strand prior to annealing with the same antisense strand. After 120 h exposure to the various agents, the cell viability was determined by addition of Cell Titer Glo (PE), plates were shaken for 10-20 mins and then luminescence signal correlating with cell viability was determined in a PE Envision plate reader. FIG. 13 shows the effect of adding additional GEMs on the 3' end of the Sense strand on efficacy and potency.

It was reasoned that, since such an improvement in efficacy against pancreatic cancer cell viability was obtained when adding 2 GEM nucleotides onto the SS of an siRNA, then adding additional GEMs would further improve the efficacy and/or potency of the siRNAs. To this end the unmodified 19mer siRNA (CHK-AZ) was compared with the same sequence where 2Gems were added at the 3' end of the SS (poly-2), 4GEMs were added (poly-4) or 6 GEMs were added (poly-6). These sequences were compared with gemcitabine alone (GEM). The experiment was performed by transfection of the siRNAs in BxPC3 cells as for FIG. 1 but the exposure time prior to measurement of cell viability was 120 h. Because of the longer incubation time the dose response of the siRNAs was explored at much lower concentrations. This enabled a true $IC_{50}$ value to be ascertained. GEM itself produced a full dose response in this cell line and at this incubation time produced a 3 nM $IC_{50}$ with 100% reduction in cell viability at concentrations above 50 nM. Unmodified 19mer siRNA (CHK-AZ) gave an $IC_{50}$ of 0.16 nM. However, the efficacy maxed out at ~70% inhibition of cell viability—even at this prolonged exposure time. Adding 2, 4 or 6 Gems to the 3' end of the siRNA all improved maximal efficacy of the product so that cell viability was less than 10% at concentrations above 10 nM. However, the expectation that more GEMs would improve the potency of the siRNAs was not met and a sequence with 2 GEMs was more potent than either the 4 Gem or 6 Gem constructs. The 2 GEM construct showed an improvement in IC50 (0.026 nM) relative to gemcitabine alone (3 nM) of 115 fold. These data suggest that more than 2 GEMs at the 3'end of a SS of an siRNA had no additional effect on potency or efficacy of the constructs in a cell viability assay.

Example 4

BxPC3 cells ($2.5 \times 10^5$ cells/well of 12-well plate) were transfected with different variants of Chk1/Gem siRNA (50 nM). 24 hrs after transfection, the relative level of Chk1 RNA was determined by Sybr Green RT-PCR. The expression level of B-actin was used as a normalizer. mRNA level in all samples was calculated relative to that in non-treated cells with the $\Delta\Delta Ct$ method.

2AGem/Chk—2 Gemcitabines replacing Cs on antisense strand of CHK1 siRNA

2AGem/NS—2 Gemcitabines replacing Cs on antisense strand of non-silencing siRNA

2SGem/Chk—2 Gemcitabines replacing Cs on sense strand of CHK1 siRNA

2SGem/NS—2 Gemcitabines replacing Cs on sense strand of non-silencing siRNA

4Gem/CHK—2 Gemcitabines replacing Cs on sense strand of CHK1 siRNA and 2 gemcitabines replacing Cs on antisense strand of CHK1 siRNA 4Gem/NS—2 Gemcitabines replacing Cs on sense strand of non-silencing siRNA and 2 Gemcitabines replacing Cs on antisense strand of non-silencing siRNA Blnk—untreated samples Chk_Az(a)—unmodified CHK1 siRNA NS—Non silencing siRNA alone.

Figure 14:
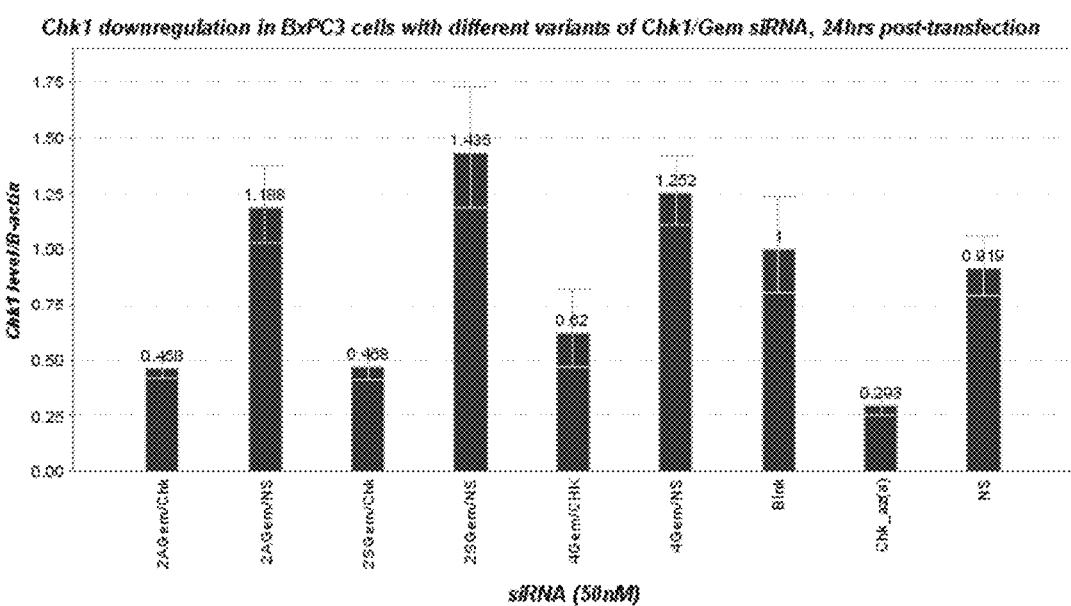
FIG. 14 shows CHK1 downregulation in BxPC3 cells with different variants of CHK1/GEM siRNA, 24 hours post-transfection.

FIG. 14 shows the effect of inserting gemcitabines within the sense/antisense strands and the effect on gene silencing (qPCR results).

Example 5

Figure 15:
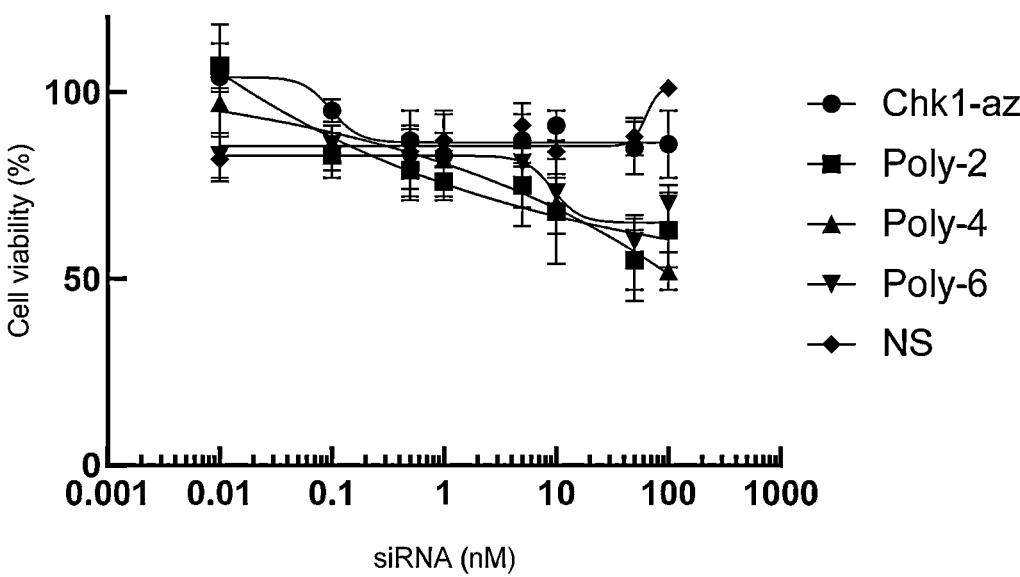
FIG. 15(a)-(c) show BxPC3 cell viability (a) 48 hours, (b) 72 hours and (c) 120 hours post-transfection for a variety of siRNAs (CHK1-az; Poly[GEM]-2; Poly-4; Poly-6) and NS control and GEM in (c).
Figure 15:
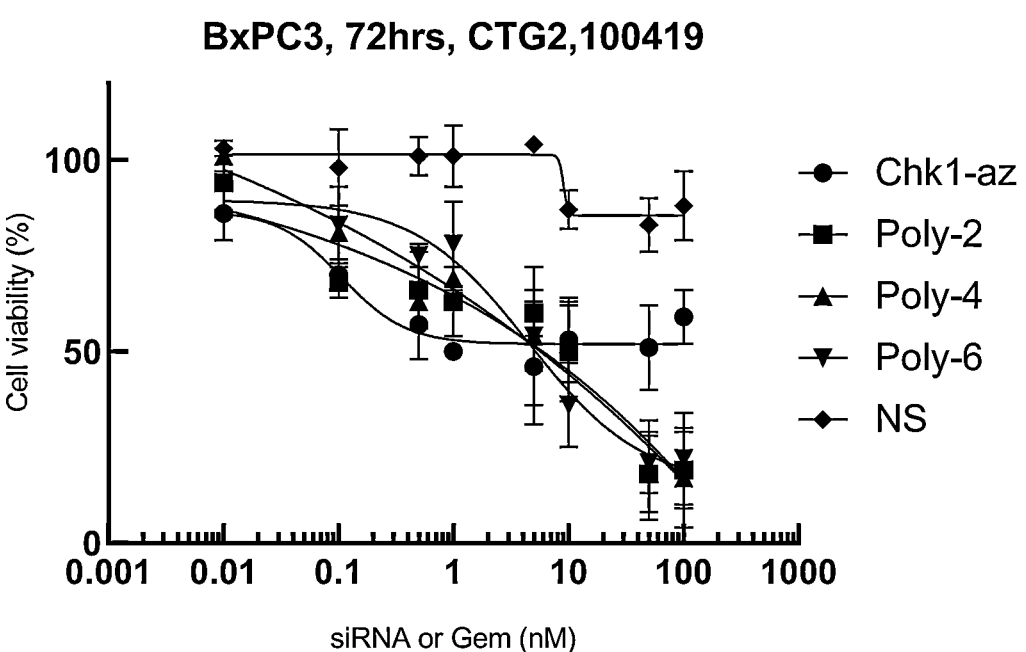
Figure 15:
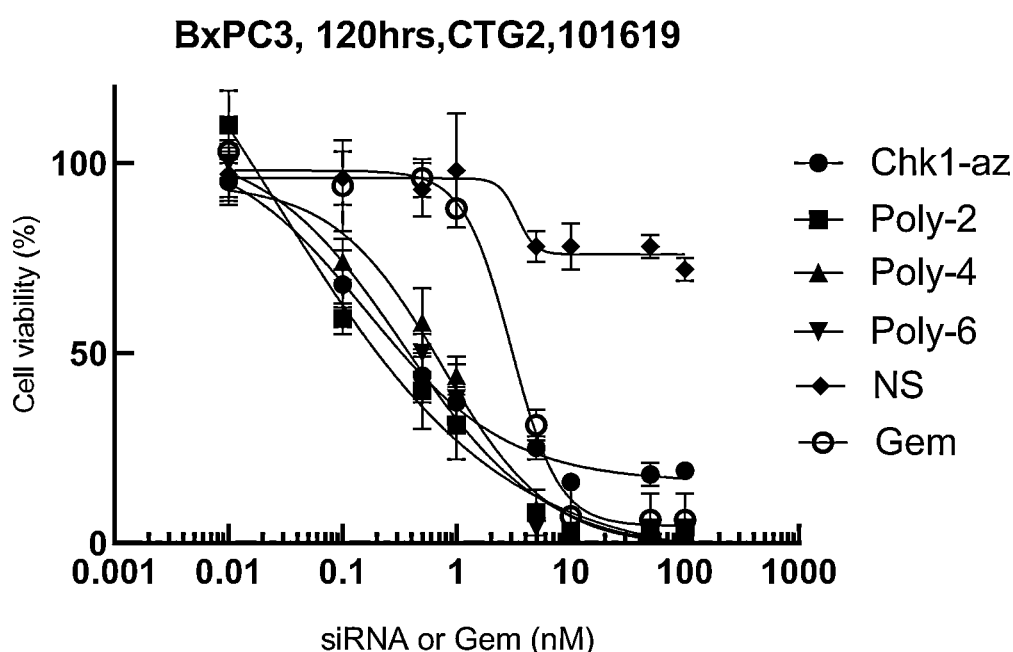

The results observed with the GEM modified siRNAs in BxPC3 cells was dependent on the time of exposure to these agents. FIG. 15 shows the time dependence of efficacy with siRNA and siRNA-GEM constructs in cell viability. Viability of cells exposed to the compounds was examined at varying concentrations at 48 h (left panel), 72 h (middle panel) or 120 h (right panel). It can be seen at each time point, the unlabeled siRNA (CHK-Az) showed a weaker effect at the highest concentration (100 nM) than the GEM-modified siRNAs (poly-2, poly-4 or poly-6—with 2, 4 or 6 gemcitabine moieties included at the 3' end). While there was not much difference in potency or efficacy between the siRNA containing 2 Gems (poly-2) compared with 4 (poly-4) or 6 Gems (poly-6), the degree of cell killing by each of the polyGEM constructs increased with time of exposure (from ~40% at 48 h, to ~70% at 72 h and 100% at 120 h). This data suggests that only 1 or 2 gemcitabine molecules were released per siRNA entering the cell. Furthermore, the time dependence may reflect the time it takes to obtain robust gene silencing to augment the effect of the GEMs themselves or it may suggest that the process required to activate released GEMs also takes time. This is the time needed for release of the gemcitabine moiety and then the triple phosphorylation of the nucleotide required in order to produce the active moiety that can block the replication fork through incorporation of the nuclease stable GEM nucleoside into the extending sequence. It could also be dependent on the cell cycle and dividing (replication) time for the specific cell type—for BxPC3 this is ~48-60 hours so at 120 h we will have gone through 2-3 division cycles compared with 1 at 72 h.

Example 6

Figure 16:
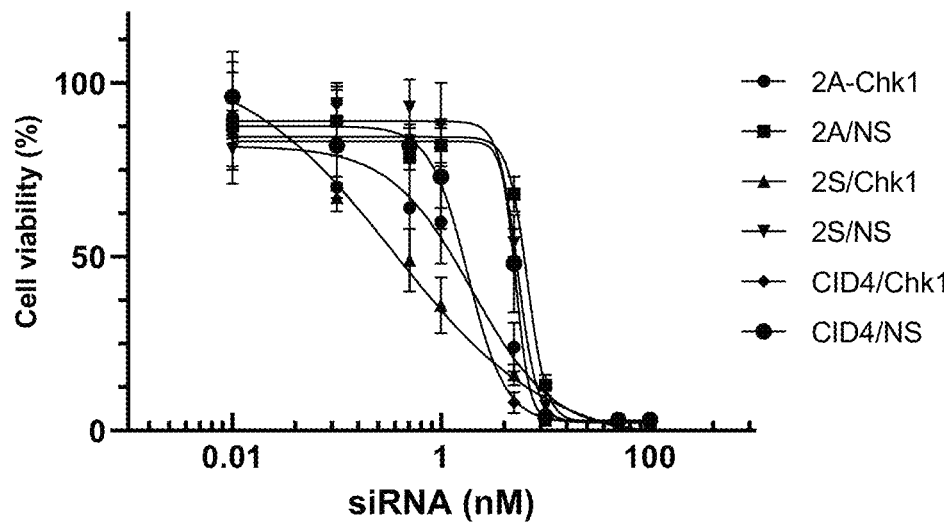
FIG. 16 shows BxPC3 cell viability 120 hours post-transfection for 2A-CHK1, 2S/CHK1 and CID4/CHK1, and their NS controls.

We further determined whether the GEM nucleotide could be used to replace the Cytidine nucleotides within the siRNA in the antisense (AS) strand of the siRNA. To explore this we again used the 19mer siRNA sequence against CHK1 from Azorsa et al. In FIG. 16:

2A-CHK1 refers to 2 GEMS replacing the Cs in the AS strand of the siRNA silencing CHK1

2A/NS refers to 2 GEMs replacing the Cs in a Non-Silencing (NS) siRNA sequence

2S/Chk1 refers to 2 GEMs replacing the Cs in the Sense Strand of the siRNA against CHK1.

2S/NS refers to 2 GEMs replacing the Cs in the Sense Strand of the Non-Silencing (NS) siRNA.

CID4/Chk1 refers to the CHK1 siRNA where both the SS and the AS strands each contained 2 Gems—making a single siRNA with 4 GEMs present.

CID4/NS refers to the Non-Silencing (NS) siRNA where both the SS and the AS strands each contained 2 Gems—making a single siRNA with 4 GEMs present upon annealing.

Each of these constructs were transfected into BxPC3 cells in 384 well plates at a density of 1000 cells per well. Cells were subsequently incubated at 37 C in 5% $CO_2$ and 95% humidity for 120 h post-transfection prior to measurement of cell viability using Cell Titer Glo (PE) as described previously.

This experiment showed that incorporating 2 GEMs into the SS of the siRNA targeting CHK1 (2S/Chk1) gave the combined effect of silencing this gene and the effect of releasing gemcitabine within the cells—producing a shift in the IC50 (0.35 nM) while also maintaining full efficacy. This compared with the incorporation of 2 GEMs into the SS of the Non-Silencing (NS) siRNA where we do not get the benefit of silencing CHK1 to see synergy with the release of the GEMs but we see only the effect of GEM release on the apparent IC50 (5.4 nM). Therefore just adding 2 Gems to the Chk1 siRNA we see ~15 fold improvement over having 2 GEMs in a NS siRNA SS.

Adding 2 GEMs in the AS strands of CHK1 and NS siRNAs we see that the CHK1-GEM IC50 (2A-Chk1) was reduced to 1.975 nM compared with the NS siRNA (2A/Ns) at 6.68 nM. This suggests that having GEMs in the AS sequence of the CHK1 can still produce some efficacy compared with NS-GEM but the differential in effect is only 3 fold and inserting GEMs in the AS strand of CHK1 resulted in a decrease in potency of ~6-fold compared with the 2 GEMs in the SS. This suggests that the GEMs in the AS strand are interfering with the silencing capabilities of the AS strand—so we do not get the augmentation induced by silencing the CHK1 gene. The IC50 for the combination of siRNA strands where both the CHK1 AS and SS strands each have 2 GEMs incorporated (CID4/Chk1; 1.8 nM) is very close to the IC50 for the siRNA incorporating the 2Gems only in the AS strand (2A-Chk1; 1.98 nM). This suggests that there is little benefit from adding 4 Gems and we see the same potency as when we have 2 GEMs in the SS. This is consistent with the expectation that the AS strand is held intact in the RISC complex for gene silencing (but the Gems on this strand prevent good silencing) while the 2 GEMs on the Sense strand (that is unwound from the AS strand when this is incorporated into RISC and is then cleaved by nucleases in the cytoplasm) are released and contribute to the maximal activity observed. This is consistent even for the NS siRNA since the 2S/NS IC50 (5.4 nM) is very similar to that for CID4/NS IC50 (5.19 nM).

The curves for 2S/NS, 2A/NS and CID4/NS all overlap and have a much lower IC50 than those where CHK1 was silenced. The former siRNAs have no gene silencing and therefore all of their effect is solely due to release of the 2 GEMs present on the SS during cleavage—providing similar $IC_{50}$ values and effects comparable to the dose response for gemcitabine alone (see FIG. 13 and FIG. 14). FIG. 16 shows the effect of including GEMs in place of Cs in the AS strand.

Example 7

TABLE 1

| Structures of polyGEM Chk1-Az siRNA sequences | | | |
|---|---|---|---|
| Label | Oligos | Duplex (µM) | Purity HPLC |
| CHK1_2eGemCHK1_S_2Gem + CHK1_dTdT_AS | 260.8 | AZ_CHKI_sense 2GEM3' 5'-AAG-AAA-GAG-AUC-UGU-AUC-AAU-(2 x 2'FC-gem)- dTdT-3' (SEQ ID NO: 15) | 82% |
| CHK1_4eGemCHK1_S_4Gem + CHK1_dTdT_AS | 415.0 | AZ_CHKI_sense 4GEM3' 5'-AAG-AAA-GAG-AUC-UGU-AUC-AAU-(4 x 2'FC-gem)-dTdT-3' (SEQ ID NO: 16) | 81% |
| CHK1_6eGemCHK1_S_6Gem +CHK1_dTdT_AS | 233.0 | AZ_CHKI_sense 6GEM3' 5'-AAG-AAA-GAG-AUC-UGU-AUC-AAU-(6 x 2' FC-gem)-dTdT-3' (SEQ ID NO: 17) | 75% |

The table below shows the sequences of the Sense strands for the polyGEM constructs used with the Azorsa 19mer siRNA. 2, 4 or 6 Gem nucleotides were inserted in the SS at the 3' end of the siRNA before the dTdT 2 base overhang. After synthesis, purity of each oligo was assessed solely due to release of the 2 GEMs d by HPLC and we observed purity of 75-82% for each of the 3 oligos (right column). Each of these sequences (or the same SS without any GEMs added) were then annealed with the corresponding base matching AS strand to form the siRNA duplex. The concentration of each duplex was determined by A260/A280 measurements and is shown in the 3rd column.

The siRNA sequences shown in Table 2 were tested for efficacy and potency against BxPC3 pancreatic cancer cell viability after 120 h exposure. The figure above shows the effect of titrating gemcitabine alone (GEM) on the viability of the BxPC3 cells determined after a 120 h exposure. The IC50 was ~5 nM but maximal efficacy was only ~85% inhibition of cell viability—even at 100 nM.

Unmodified siRNA against RAD17 (SL-P49-3) showed a dose dependent decrease in cell viability with an IC50 of ~4 nM and a maximal efficacy of only 60% inhibition of cell

TABLE 2

Sequences of Sense strand and Antisense strands for siRNAs tested for efficacy and potency

| Sample | Label | Target | SENSE STRAND | ANTISENSE STRAND |
|---|---|---|---|---|
| 1 | SLP49-1 | CHK1 | 5'-CCUGUGGAAUAGUACUUA-CUGCAAU-3' (SEQ ID NO: 18) | 5'-AUUGCAGUAAGUACUAU-UCCACAGG-3' (SEQ ID NO: 25) |
| 2 | SLP49-2 | CHK1 | 5'-CCUGUGGAAUAGUACU UAC-UGCAAU[GEM] [GEM]-3' (SEQ ID NO: 19) | 5'-AUUGCAGUAAGUACUAU-UCCACAGG-3' (SEQ ID NO: 25) |
| 5 | SLP49-5 | CHK1 | 5'__U GUG GAA U AG UA[GEM] UUA [GEM]UG [GEM]AA U-3' (SEQ ID NO: 20) | 5'-AUUGCAGUAAGUACUA-UUCCACAGG-3' (SEQ ID NO: 25) |
| 6 | SLP49-6 | CHK1 | 5'__U GUG GAA U AG UAC UUA CUG CAA U [GEM] [GEM]-3' (SEQ ID NO: 21) | 5'-AUUGCAGUAAGUACUAU-UCCACAGG-3' (SEQ ID NO: 25) |
| 7 | SLP49-7 | CHK1 | 5'-[GEM] [GEM] U GUG GAA U AG UAC UUA [GEM]UG [GEM]AA U-3' (SEQ ID NO: 22) | 5'-AUUGCAGUAAGUACUAU U-CCACAGG-3' (SEQ ID NO: 25) |
| 3 | SLP49-3 | RAD 17 | 5'-CCAACAAUUAUGAUGAAAUU UCUUA-3' (SEQ ID NO: 23) | 5'-UAAGAAAUUUCAUCAUA A-UUGUUGG-3' (SEQ ID NO: 26) |
| 4 | SLP49-4 | RAD 17 | 5'-CCAACAAUUAUGAUGAA A-UUUCUUA-[GEM] [GEM]3' (SEQ ID NO: 24) | 5'-UAAGAAAUUUCAUCAUA A-UUGUUGG-3' (SEQ ID NO: 26) |

The sequences above were used to anneal to generate duplex 25mer blunt ended siRNAs. Sequence 1 is the 25mer blunt ended siRNA without any GEM incorporated into the SS sequence. Sequence 2 has 2 GEMs attached at the 3' end of the Sense Strand which is then annealed with the same AS strand as in sequence #1. Sequences 5 and 6 are the same AS strand but where the first 2 bases of the SS are removed to shorten the sequence (this is aimed at trying to force the use of the other strand as the AS strand). Sequences 5 and 6 vary in that sequence 6 does not contain a GEM in place of the Cytidine group at position 13 of seq5 (or position 15 in the original SS sequence). The rationale for this exclusion was to determine whether inserting a GEM at this location blocked the cleavage of the SS that may be required for loading the AS strand into the RISC complex during silencing. Sequence 7 is the same as Sequence 6 but includes 2 GEMs in place of the 2 Cytidines present at the 5' terminus of the SENSE strand (to see if adding more GEMs per siRNA resulted in improved potency or efficacy of the final construct). Sequence 3 is an unlabeled 25mer blunt ended siRNA against RAD17 while Sequence 4 is the same siRNA but with 2 additional GEMs attached at the 3' end of the SS.

viability. When this siRNA had 2 gemcitabine moieties added at the 3' end of the Sense Strand, we see a dramatic improvement in efficacy (100% cell killing at 30 nM) with no change in the potency (IC50 ~4 nM).

A 25mer blunt ended siRNA sequence was demonstrated to have a very potent effect on cell killing when used without GEM modification (SL-P49-1; IC50 0.25 nM and Efficacy 90% at 100 nM).

Like RAD17, adding 2 Gems to the 3' end of the SS resulted in a product (SL-P49-2) with a similar IC50 value but greater efficacy (~100% inhibition at 30 nM).

Figure 17:
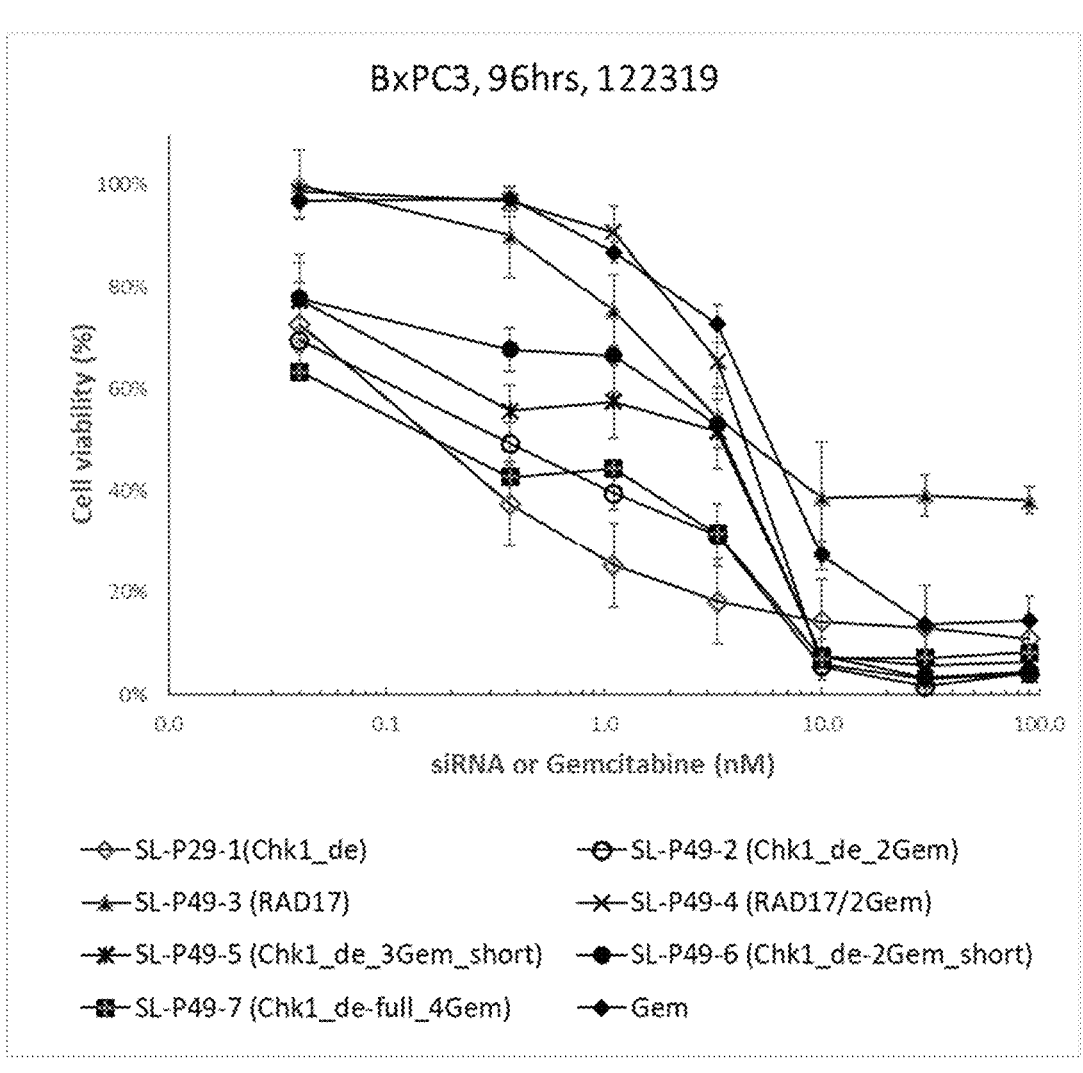
FIG. 17 shows BxPC3 cell viability 96 hours post-transfection for various siRNA molecules (P49-1, P49-2, P49-3, P49-4, P49-5, P49-6, P49-7 and GEM).

FIG. 17 shows the effect of GEM position and number of modifications in the SS of the siRNA on efficacy and potency of the siRNA/Gem combination.

Shortening the 5' end of the SS of the CHk1 siRNA containing either 2 Gems (SL-P49-6) or 3Gems (SL-P49-5) resulted in the same effect (IC50 ~3 nM; Maximal efficacy of 83-97% at 30 nM). This suggests a mediocre silencing effect augmented by release of a single GEM form either siRNA.

Using the same SS sequence with 4 GEMs included in place of the Cs (SL-P49-7) gave similar IC50 and efficacy values to the sequence containing just 2 GEMs (SL-49P-2). This result suggests that this siRNA Antisense Strand sequence is providing the maximal amount of gene silencing but the GEM released from the SS containing either 2 or 4 Gems produces the same improvement in efficacy—suggesting that releasing 4 Gems does not improve efficacy compared with 2 so there must be a saturation of the effect by Gems. It is possible that beyond 1 Gem per molecule there is no further cleavage of the GEMs to produce additive effects. We thought that the exonucleases may not be able to cleave and release a second GEM when it was directly attached to another GEM in the same sequence (e.g. in SL-P49-2 in Table 2 and the above figure). However, even when we separated the GEMs by nuclease sensitive nucleotides (e.g. in SL-49P-5 or SL-49P-7), we did not see any further improvement in potency or efficacy. The results suggest that only a single Gem may provide the effects seen. This may be as a result of the time required to release the SS from the AS strand during the siRNA RISC loading, the degradation of the SS in the cytoplasm with release of GEMs that then require phosphorylation to insert into the replicating DNA fork structure. Alternatively, the amount of GEMs released may correlate with the cell replication cycle and hence be limiting in terms of the rate of Gem incorporation into the forks.

Example 8

Figure 18:
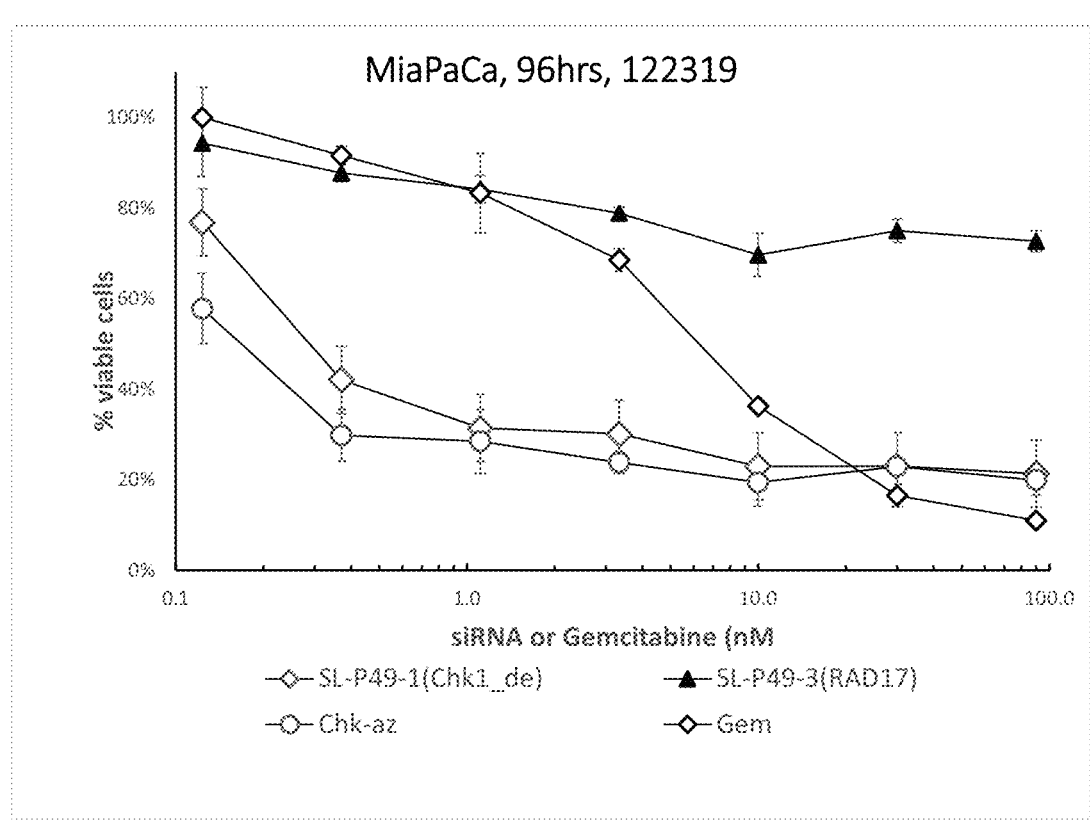
FIG. 18 shows MiaPaCa pancreatic cancer cell viability 96 hours post-transfection for P49-1 (CHK1_de), P49-3 (RAD17), CHK-az, and GEM.

Using gemcitabine or the same unmodified siRNAs and exposure time (96 h) as used against BxPC3 cells (FIG. 1), we studied the effect on another pancreatic cancer cell line—MiaPaca-2. Like in BxPC3 cells, gemcitabine alone produced a dose dependent decrease in cell viability with a similar IC50 value and maximal efficacy. While the 19mer siRNA (CHK-Az) and the 25mer blunt ended siRNA designed against CHK1 both showed similar efficacy (maximal inhibition ~80%) this was much greater than the 60% inhibition observed for the 19mer in BxPC3 cells but similar for the 25mer against these cells. The RAD17 siRNA however showed much reduced efficacy when used alone against the MiaPaca cells (maximum inhibition of only ~30%) than against BxPC3 cells (maximal inhibition of ~60%). FIG. 18 shows the effect of constructs in another pancreatic tumor cell—MiaPaca.

Example 9

Figure 19:
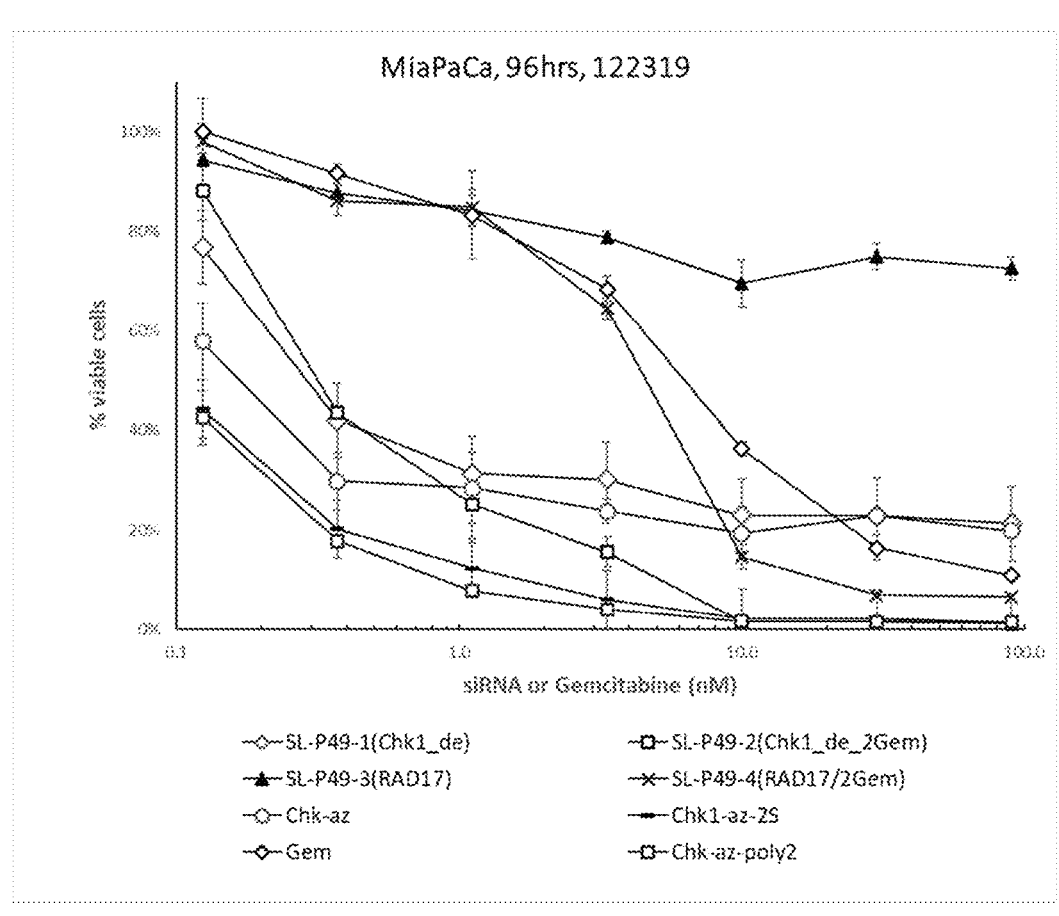
FIG. 19 shows MiaPaCa pancreatic cancer cell viability 96 hours post-transfection for P49-1 (CHK1_de), P49-2 (CHK1_de_2GEM); P49-3 (RAD17); P49-4 (RAD17/2GEM); CHK-az, and GEM.

In MiaPaca cells the 2 unmodified siRNAs, Chk1_de (the 25mer blunt ended sequence) or Chk-Az (19mer with 2 base dTdT overhang) showed similar maximal efficacy of 80% inhibition. Addition of 2 GEMs to the CHK1-Az sequence—either on the 3' end of the SS (Chk-az-poly2) or by replacement of the Cs within the SS (Chk1-AZ-2S) resulted in a significant improvement in efficacy of the siRNA in killing MiaPaca cells (maximal inhibition ~100% at 10 nM). The same was true for the addition of 2 GEMs on the 3' end of the SS of the 25-mer siRNA (Chkde_2Gem) which also resulted in maximal efficacy at 10 nM at ~100% versus MiaPaca cells. While the unmodified 25mer siRNA targeting RAD17 showed almost no efficacy against MiaPaca cell viability (maximal ~25%), addition of 2Gems to the 3' end of the SS of this siRNA dramatically improved the efficacy of this construct (inhibition of 93% at 30 nM). ALL modified siRNAs now showed a maximal efficacy beyond that achievable using gemcitabine alone (maximal inhibition of 90% at 100 nM). FIG. 19 shows the effects of Gem modified siRNAs on MiaPaca cells.

Although this invention has been described in relation to certain embodiments thereof, and many details have been set forth for purposes of illustration, it will be apparent to those skilled in the art that the invention is susceptible to additional embodiments and that certain of the details described herein may be varied without departing from the basic principles of the invention.

The invention claimed is:

1. An siRNA comprising a sense strand having the sequence:

```
                              (SEQ ID NO: 18)
    5'-CCU GUG GAA UAG UAC UUA CUG CAA U-3'
``` and an antisense strand having the sequence

```
                              (SEQ ID NO: 2)
    5'-A UUG CAG UAA GUA CUA UUC CAC AGG-3',
``` wherein one or more cytosine moieties within the sense strand are replaced by a gemcitabine moiety.

2. The siRNA of claim 1, wherein said sense strand has the sequence:

```
                              (SEQ ID NO: 18)
SS = 5'-CCU GUG GAA UAG UAC* UUA C*UG C*AA U-3',
``` wherein C* represents a cytosine moiety replaced by a gemcitabine moiety.

3. An siRNA sequence against mouse and human genes for RAD17, wherein the sense strand (SS) is

```
RAD17_7(6):
                              (SEQ ID NO: 23)
    SS-5'CCAACAAUUAUGAUGAAAUUUCUUA-3'
``` and wherein one or more cytosine moieties within the sense strand are replaced by a gemcitabine moiety.

4. The siRNA of claim 3, wherein sense strand of the siRNA comprises the sequence:

```
                              (SEQ ID NO: 32)
    SS-5'CCAAC*AAUUAUGAUGAAAUUUC*UUA-3'
``` wherein C* represents a cytosine moiety replaced by a gemcitabine moiety.

5. A composition comprising the siRNA of claim 1 and a pharmaceutically acceptable carrier.

6. The composition of claim 5, wherein the pharmaceutically acceptable carrier comprises a branched histidine-lysine co-polymer.

7. A composition comprising the siRNA of claim 3 and a pharmaceutically acceptable carrier.

8. The composition of claim 7, wherein the pharmaceutically acceptable carrier comprises a branched histidine-lysine co-polymer.

9. The siRNA of claim 1, wherein the siRNA is chemically modified and attached directly to a targeting ligand that comprises GalNac.

10. The siRNA of claim 3, wherein the siRNA is chemically modified and attached directly to a targeting ligand that comprises GalNac.

\* \* \* \* \*